(12) United States Patent
Nakatsuji et al.

(10) Patent No.: US 8,658,425 B2
(45) Date of Patent: Feb. 25, 2014

(54) METHOD FOR PROMOTING DIFFERENTIATION OF PLURIPOTENT STEM CELLS INTO CARDIAC MUSCLE CELLS

(71) Applicant: Kyoto University, Kyoto (JP)

(72) Inventors: Norio Nakatsuji, Kyoto (JP); Motonari Uesugi, Kyoto (JP); Kouhei Yamada, Kyoto (JP); Itsunari Minami, Kyoto (JP); Tomomi Otsuji, Kyoto (JP)

(73) Assignee: Kyoto University, Kyoto-shi (JP)

( * ) Notice: Subject to any disclaimer, the term of this patent is extended or adjusted under 35 U.S.C. 154(b) by 0 days.

(21) Appl. No.: 13/777,765

(22) Filed: Feb. 26, 2013

(65) Prior Publication Data
US 2013/0183753 A1    Jul. 18, 2013

Related U.S. Application Data

(63) Continuation of application No. PCT/JP2011/069054, filed on Aug. 24, 2011.

(30) Foreign Application Priority Data

Aug. 26, 2010   (JP) ................................ 2010-189548

(51) Int. Cl.
C12N 5/02    (2006.01)
(52) U.S. Cl.
USPC ........... 435/377; 435/363; 435/243; 514/135; 514/368; 548/163
(58) Field of Classification Search
USPC .................. 435/377, 363, 243; 544/368, 135; 548/163
See application file for complete search history.

(56) References Cited

U.S. PATENT DOCUMENTS

| | | | |
|---|---|---|---|
| 2003/0134859 A1 | 7/2003 | Amemiya et al. | |
| 2007/0134215 A1* | 6/2007 | Fukuda et al. | 424/93.21 |
| 2007/0148185 A1 | 6/2007 | Rathore et al. | |
| 2007/0149466 A1 | 6/2007 | Milburn et al. | |
| 2009/0068742 A1 | 3/2009 | Yamanaka | |
| 2009/0170914 A1 | 7/2009 | Bornancin et al. | |
| 2012/0244619 A1 | 9/2012 | Nakatsuji et al. | |

FOREIGN PATENT DOCUMENTS

| | | |
|---|---|---|
| JP | 2001-510450 A | 7/2001 |
| JP | 2004-535199 A | 11/2004 |
| JP | 2005-330443 A | 12/2005 |
| JP | 2006-218035 A | 8/2006 |
| JP | 2007-252220 A | 10/2007 |
| JP | 2009-500357 A | 1/2009 |
| JP | 2009-531365 A | 9/2009 |
| WO | WO-98/17267 | 4/1998 |
| WO | WO-01/83427 A1 | 11/2001 |
| WO | WO-03/006950 A2 | 1/2003 |
| WO | WO-2005/037845 A1 | 4/2005 |
| WO | WO-2007/069666 A1 | 6/2007 |
| WO | WO-2008/118820 A2 | 10/2008 |
| WO | WO-2009/006930 A1 | 1/2009 |
| WO | WO-2009/006997 A1 | 1/2009 |
| WO | WO-2009/007852 A2 | 1/2009 |
| WO | WO-2011/002950 A1 | 1/2011 |
| WO | WO-2011/071118 A1 | 6/2011 |

OTHER PUBLICATIONS

Stuckwisch et al. J. Med. Chem. (1965) 8(5): 734-735.*
Shamblott et al., "Derivation of pluripotent sten cells from cultured human primordial germ cells", Proc. Natl. Acad. Sci. USA 1998, vol. 95, 13726-13731.
Graichen et al., "Enhanced cardiomyogenesis of human embryonic stem cells by a small molecular inhibitor of p38 MAPK", Differentiation (2008) 76:357-370.
Xu et al., "Chemically defined medium supporting cardiomyocyte differentiation of human embryonic stem cells", Differentiation (2008) 76:958-970.
Carlton et al., "Discovery of small molecule agonists for the bombesin receptor subtype 3 (BRS-3) based on an omeprazole lead", Bioorganic & Medicinal Chemistry Letters, 2008, vol. 18, No. 20, pp. 5451-5455.
Bellasio et al., "Substances with potential cardiovascular activity. 2-Acylaminobenzimidazoles with hypotensive activity", Farmaco, Edizione Scientifica, 1973, vol. 28, No. 2, pp. 164-182.
Harsanyi et al., "Reactions of acylcyanamides. I. New synthesis of 2-acylaminobenzoxazoles", Annali di Chimica (Rome, Italy), 1964, vol. 54, No. 11, pp. 1060-1065.
Database Registry [Online]: Chemical Abstracts Service, Columbus, Ohio, [retrieved on Oct. 7, 2011].
Yuasa et al., "Transient inhibition of BMP signaling by Noggin induces cardiomyocyte differentiation of mouse embryonic stem cell", Nature Biotechnology, 2005, vol. 23, No. 5, pp. 607-611.
Toyama, "ES Saibo-iPS Saibo kara no Shinkin Saibo Bunka-Seisei-Ishoku", Japanese Journal of Transplantation, 2009, vol. 44, No. 3, pp. 219-225.
Mummery et al., "Differentiation of Human Embryonic Stern Cells to Cardiomyocytes: Role of Coculture With Visceral Endoderm-Like Cells", Circulation, American Heart Association, 2003, 107, pp. 2733-2740.
Yang et al., "Human cardiovascular progenitor cells develop from a KDR1 embryonic-stem-cell-derived population", Nature, 2008, vol. 453.
Leschik et al., "Cardiac commitment of primate embryonic stem cells", Nature Protocols, 2008, vol. 3, No. 9, pp. 1381-1387.
Thomson et al., "Embryonic Stem Cell Lines Derived from Human Blastocysts", Science, 1998, 282, pp. 1145-1147.
Suemori et al., "Efficient establishment of human embryonic stem cell lines and long-term maintenance with stable karyotype by enzymatic bulk passage", Biochemical and Biophysical Research Communications, 2006, 345, pp. 926-932.

(Continued)

Primary Examiner — Susan Hanley
(74) Attorney, Agent, or Firm — Fox Rothschild LLP

(57) ABSTRACT

The present invention relates to a composition for promoting differentiation of pluripotent stem cells into cardiac muscle cells, and a method for inducing differentiation of pluripotent stem cells into cardiac muscle cells and a method for preparing cardiac muscle cells.

15 Claims, 17 Drawing Sheets

(56) References Cited

OTHER PUBLICATIONS

Thomson et al., "Isolation of a primate embryonic stem cell line", Proc. Natl. Acad. Sci. USA, 1995, vol. 92, pp. 7844-7848.
Thomson et al., "Pluripotent Cell Lines Derived from Common Marmoset (*Callithrix jacchus*) Blastocysts", Biology of Reproduction, 1996, 55, pp. 254-259.
Doetschman et al., "Establishment of Hamster Blastocyst-Derived Embryonic Stem (ES) Cells", Developmental Biology, 1988, 127,224-227.
Evans et al., "Derivation and Preliminary Chabacterization of Pluripotent Cell Lines From Porcine and Bovine Blastocysts", Theriogenology, 1990, vol. 33, No. 1, pp. 125-128.
Piedrahita et al., "On the Isolation of Embryonic Stem Cells: Comparative Behavior of Murine, Porcine and Ovine Embryos", Theriogenology, 1990, vol. 34, No. 5, pp. 879-891.
Notarianni et al., "Maintenance and differentiation in culture of pluripotential embryonic cell lines from pig blastocysts", Journals of Reproduction & Fertility, 1990, 41, pp. 51-56.
Talbot et al., "Culturing the epiblast cells of the pig blastocyst", In Vitro Cell. Dev. Biol., 1993 29A, pp. 543-554.
Notarianni et al., "Derivation of pluripotent, embryonic cell lines from the pig and sheep", J. Reprod. Fert., 1991, 43, pp. 255-260.
Saito et al., "Bovine embryonic stem cell-like cell lines cultured over several passages", Roux's Arch Dev Biol, 1992, 201, pp. 134-141.
Sukoyan et al., "Isolation and Cultivation of Blastocyst-Derived Stem Cell Lines From American Mink (Mustela vision)", Molecular Reproduction and Development, 1992, 33, pp. 418-431.
Shi et al., "Induction of Pluripotent Stem Cells from Mouse Embryonic Fibroblasts by Oct4 and Kll4 with Small-Molecule Compounds", Cell Stem Cell, 2008, 3, pp. 568-574.
Zhou et al., "Generation of Induced Pluripotent Stem Cells Using Recombinant Proteins", Cell Stem Cell, 2009, 4, pp. 381-384.
Kim et al., "Pluripotent stem cells induced from adult neural stem cells by reprogramming with two factors", Nature, 2008, vol. 454, pp. 646-650.
Kim et al., "Oct4—Induced Pluripotency in Adult Neural Stem Cells", Cell, 2009, 136, pp. 411-419.
Huangfu et al., "Induction of pluripotent stem cells from primary human fibroblasts with only Oct4 and Sox2", Nature Biotechnology, 2008, vol. 26, pp. 1269-1275.
Zhao et al., "Two Supporting Factors Greatly Improve the Efficiency of Human iPSC Generation", Cell Stem Cell, 2008, 3, pp. 475-479.
Feng et al., "Reprogramming of fibroblasts into induced pluripotent stem cells with orphan nuclear receptor Esrrb", Nature Cell Biology, 2009, vol. 11, pp. 197-203.
Hanna et al., "Direct Reprogramming of Terminally Differentiated Mature B Lymphocytes to Pluripotency", Cell, 2008, 133, pp. 250-264.
Takahashi et al., "Induction of Pluripotent Stem Cells from Adult Human Fibroblasts by Defined Factors", Cell, 2007, 131, pp. 861-872.
Yu et al., "Cells Induced Pluripotent Stem Cell Lines Derived from Human Somatic", Science, 2007, 318, 1917-1920.
English translation of the International Preliminary Report on Patentability issued Mar. 19, 2013 in corresponding International Application Serial No. PCT/JP2011/069054.
SciPlanner 2013. Chemical Abstracts Service, Columbus, OH; RN-349132-98-5, download Sep. 27, 2013.
SciPlanner 2013. Chemical Abstracts Service, Columbus, OH; RN-1118807-13-8, download Sep. 24, 2013.

\* cited by examiner

Cardiac muscle cells derived from monkey ES cells

Increase rate of GFP fluorescence intensity (%)

METHOD FOR PROMOTING DIFFERENTIATION OF PLURIPOTENT STEM CELLS INTO CARDIAC MUSCLE CELLS

CROSS-REFERENCE TO RELATED APPLICATIONS

This application is a continuation of, and claims the benefit of, PCT Application No. PCT/JP2011/069054 filed Aug. 24, 2011 and claims priority to Japanese Patent Application Number 2010-189548 filed Aug. 26, 2010, the disclosures of which are hereby incorporated by reference in their entireties.

TECHNICAL FIELD

The present invention relates to a composition for promoting differentiation of pluripotent stem cells into cardiac muscle cells, and a method for inducing differentiation of pluripotent stem cells into cardiac muscle cells, and a method for preparing cardiac muscle cells from pluripotent stem cells.

BACKGROUND ART

A technology to induce differentiation of pluripotent stem cells holds the key for realization of regenerative medicine and establishment of in vitro drug screening study or evaluation of drug safety. In particular, it is important for the generative medicine and drug evaluation for heart diseases because heart diseases are the second cause of death in Japan now. There are various drugs which induce severe side effects, including cardiac arrest and arrhythmia, leading to increasingly-demand to provide homogenous cardiac muscle cells which are useful for cardiotoxicity study. So far, it has been reported that cardiac muscle cell differentiation of human ES cells is induced by co-culturing human ES cells and mouse feeder cells, END2 cells (Non Patent Literature 1). However, differentiation efficiency of this method is not satisfactory and it is difficult to obtain pure human cardiac muscle cells since the resulting human cardiac muscle cells are often contaminated with mouse END2 cells. It is also reported that cardiac muscle cell differentiation is induced by preparing embryoid from ES cells and adding several cytokines (fibroblast growth factor (bFGF), bone morphogenetic protein 4 (BMP4), vascular endothelial cell growth factor (VEGF), Dickkopf-1 (DKK1), Activin A) to the embryoid (Non Patent Literatures 2 and 3). This method, however, requires huge amount of cytokines and cost too much, while its differentiation efficiency is not enough.

CITATION LIST

Non Patent Literature

Non Patent Literature 1:
  Mummery, C., et al., Differentiation of human embryonic stem cells to cardiomyocytes: role of coculture with visceral endoderm-like cells. Circulation. 107(21), 2733-40 (2003).
Non Patent Literature 2:
  Yang, L., et al., Human cardiovascular progenitor cells develop from a KDR+ embryonic-stem-cell-derived population. Nature. 453(7194), 524-8 (2008).
Non Patent Literature 3:
  Leschik, J., et al., Cardiac commitment of primate embryonic stem cells. Nat. Protoc. 3(9), 1381-7 (2008).
  The above references are herein incorporated by reference.

SUMMARY OF INVENTION

Technical Problem

A method for preparing homogeneous cardiac muscle cells with high efficiency at low cost is demanded in the fields of regenerative medicine and drug discovery.

Solution to Problem

The present inventors examined 9600 library compounds for the effect of promoting differentiation of monkey ES cells into cardiac muscle cells and a low molecular compound N11474 was found to have the effect of promoting cardiac muscle cell differentiation. Further, an analog KY02111 obtained by the synthesis development of N11474 and the analogous compounds thereof were found to have the effect of promoting cardiac muscle cell differentiation. Then, the present invention has been accomplished.

The present invention provides a composition for promoting differentiation of pluripotent stem cells into cardiac muscle cells which comprises a compound represented by Formula (I):

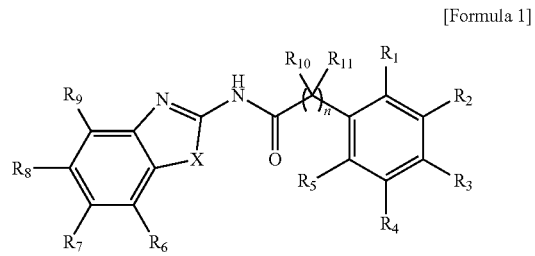

[Formula 1]

wherein
  $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—,
  $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—,
  $R_{10}$ to $R_{11}$ are each independently a hydrogen atom; or a linear or branched alkyl group having 1 to 5 carbon atoms, X is —CR$_{14}$, wherein R$_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —NR$_{15}$, wherein R$_{15}$ is a hydrogen atom, a linear or branched alkyl group having 1 to 5 carbon atoms, or a linear or branched acyl group having 1 to 5 carbon atoms, and n is an integer of 0 to 6, or a salt thereof.

In another embodiment, the present invention provides a method for inducing differentiation of pluripotent stem cells into cardiac muscle cells which comprises culturing pluripotent stem cells in a medium containing the composition for promoting differentiation of pluripotent stem cells into cardiac muscle cells as described above.

In another embodiment, the present invention provides a method for preparing cardiac muscle cells from pluripotent stem cells which comprises culturing pluripotent stem cells in a medium containing the composition for promoting differentiation of pluripotent stem cells into cardiac muscle cells as described above.

In another embodiment, the present invention provides a compound represented by Formula (I):

[Formula 2]

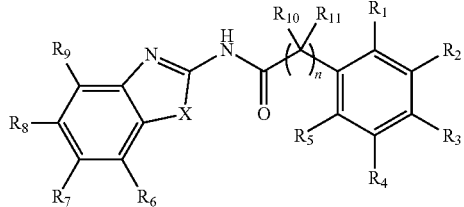

wherein

R$_1$, R$_4$ and R$_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom, R$_2$ and R$_3$ are a linear or a branched alkoxy group having 1 to 5 carbon atoms, or R$_2$ and R$_3$ join together to form —O—CH$_2$—O— or —O—(CH$_2$)$_2$—O—, R$_6$ to R$_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom; wherein two adjacent groups among R$_6$ to R$_9$ may join together to form —O—CH$_2$—C— or —O—(CH$_2$)$_2$—O—, R$_{10}$ to R$_{11}$ are each independently a hydrogen atom; or a linear or branched alkyl group having 1 to 5 carbon atoms, X is an oxygen atom; a sulfur atom; or a group —NR$_{15}$, wherein R$_{15}$ is a hydrogen atom, a linear or branched alkyl group having 1 to 5 carbon atoms, or a linear or branched acyl group having 1 to 5 carbon atoms, n is an integer of 0 to 6, with the proviso that when n is 1 or 2, R$_7$ is not Cl nor a methoxy group, R$_2$ is not a methoxy group, or a salt thereof.

Advantageous Effects of Invention

According to the present invention, it has become possible to induce differentiation of pluripotent stem cells into cardiac muscle cells without using feeder cells and obtain pure cardiac muscle cells. In addition, according to the present invention, it has become possible to induce cardiac muscle cell differentiation with higher efficiency at lower cost to prepare cardiac muscle cells than the known methods. The present invention is particularly useful for evaluation of QT prolongation which is critical for evaluation of drug safety in a high-throughput format, large-scale production of homogenous and mature human cardiac muscle cells for use in drug evaluation for heart diseases, and production of cardiac muscle cells for transplant to treat heart diseases, etc. Further, the composition of the present invention is not homologous in the molecular structure to the cardiac muscle cell differentiation promoters which have been reported so far, and the composition of the present invention is thus considered to be a totally new type of cardiac muscle cell differentiation promoter and expected to enhance the differentiation efficiency even more when used in combination with different cardiac muscle cell differentiation promoters.

BRIEF DESCRIPTION OF DRAWINGS

FIG. 5-1 illustrates the synergistic effect of promoting cardiac muscle cell differentiation between nitrovin and N11474.

FIG. 5-2 illustrates the synergistic effect of promoting cardiac muscle cell differentiation between nitrovin and KY02111.

FIG. 7-1 illustrates compounds which are effective in promoting cardiac muscle cell differentiation (1).

FIG. 7-2 illustrates the effect of promoting cardiac muscle cell differentiation of the respective compounds.

FIG. 9-1 illustrates the effects of Wnt signaling inhibitors and a Wnt signaling activator on gene expression (1).

FIG. 9-2 illustrates the effects of Wnt signaling inhibitors and a Wnt signaling activator on gene expression (2).

FIG. 11-1 illustrates the effects of a Wnt signaling activator on the effects of promoting cardiac muscle cell differentiation by KY02111, XAV939 and IWP2 (cardiac muscle cells derived from monkey ES cell).

FIG. 11-2 illustrates the effect of a Wnt signaling activator on the effect of promoting cardiac muscle cell differentiation by KY02111, XAV939, and IWP2 (human iPS cells).

DESCRIPTION OF EMBODIMENTS

Figure 1:
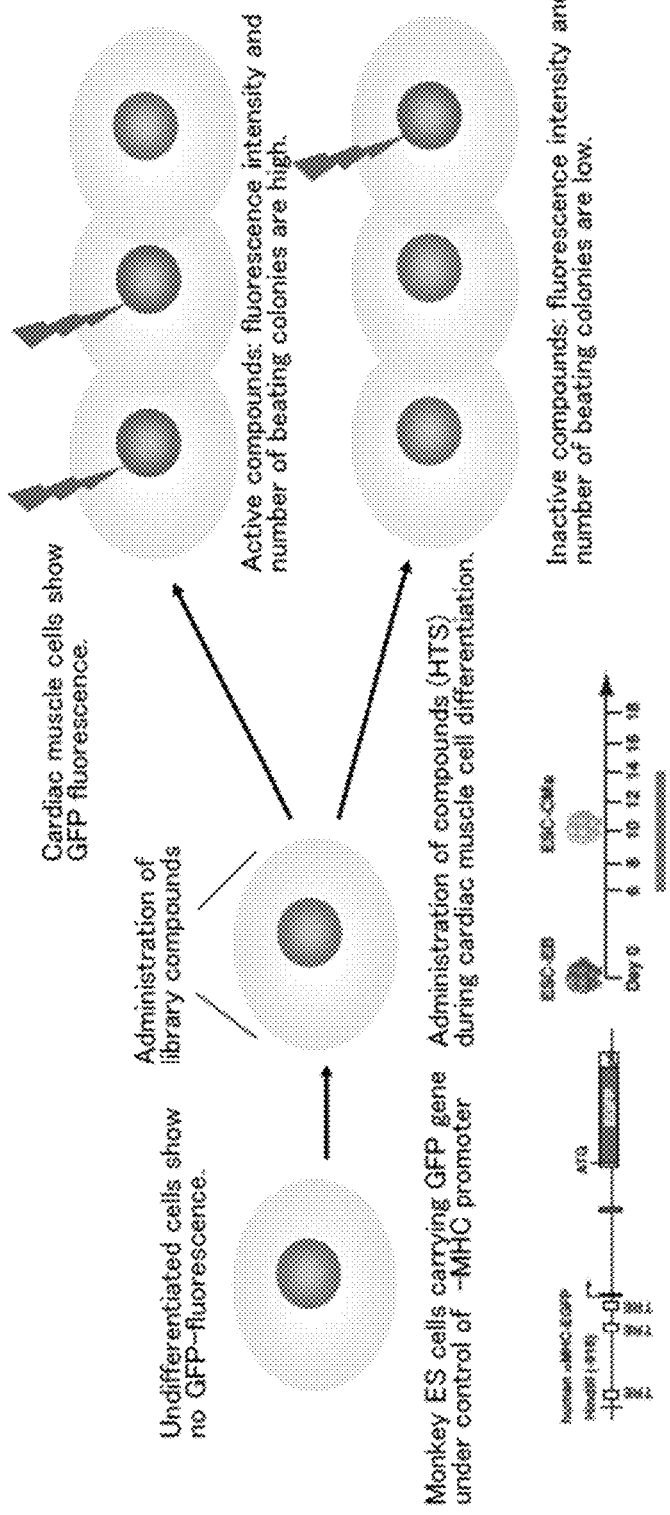
FIG. 1 illustrates a screening strategy of agents which promote cardiac muscle cell differentiation.

The present invention provides a composition for promoting differentiation of pluripotent stem cells into cardiac muscle cells containing a compound represented by Formula (I):

[Formula 3]

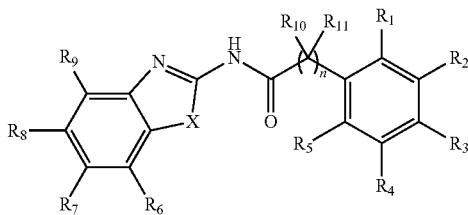

wherein $R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, or a salt thereof.

Examples of the linear or branched alkoxy group having 1 to 5 carbon atoms include a methoxy group, an ethoxy group, a propoxy group, an isopropoxy group, a butoxy group, an isobutoxy group, a sec-butoxy group, a tert-butoxy group and a pentyloxy group.

Examples of the linear or branched alkyl group having 1 to 5 carbon atoms include a methyl group, an ethyl group, a propyl group, an isopropyl group, a butyl group, an isobutyl group, a sec-butyl group, a tert-butyl group and a pentyl group.

Examples of the linear or branched acyl group having 1 to 5 carbon atoms include a formyl group, an acetyl group, a propionyl group, a butyryl group, an isobutyryl group, a valeryl group and an isovaleryl group.

Examples of the halogen atom include Cl, Br, I or F.

In a preferred embodiment, $R_1$ to $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—.

$R_2$ and $R_3$ are preferably a linear or a branched alkoxy group having 1 to 5 carbon atoms or join together to form —O—$CH_2$—O— or —O—$(CH_2)_2$—O—. Further preferably, $R_2$ and $R_3$ are a methoxy group, an ethoxy group or a propoxy group, and most preferably a methoxy group or an ethoxy group.

$R_1$, $R_4$ and $R_5$ are preferably a hydrogen atom.

In an embodiment, $R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_6$ and $R_9$ are preferably each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom, more preferably a hydrogen atom.

In a preferred embodiment, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—$CH_2$—O— or —O—$(CH_2)_2$—C—.

In an embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom, and examples of such A include a pyrrolidinyl, imidazolidinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl groups which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

$R_{10}$ and $R_{11}$ are preferably a hydrogen atom.

In a preferred embodiment, X is an oxygen atom; a sulfur atom; or a group —$NR_{15}$, wherein $R_{15}$ is a hydrogen atom, a linear or branched alkyl group having 1 to 5 carbon atoms, a linear or branched acyl group having 1 to 5 carbon atoms. X is preferably a sulfur atom.

In a preferred embodiment, n is an integer of 0 to 4. In another preferred embodiment, n is an integer of 1 to 6, an integer of 1 to 4, or 2 or 3.

In a preferred embodiment, the composition of the present invention contains the compound selected from the following group or a salt thereof:

[Formula 4]

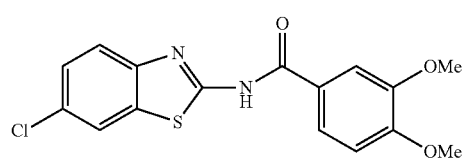

KY01041

[Formula 5]

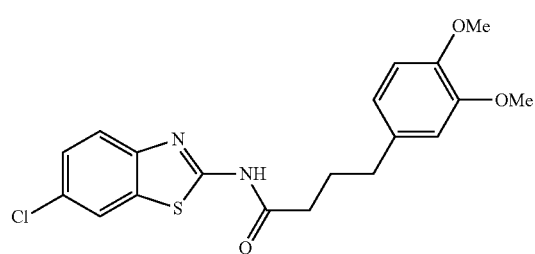

T61164

[Formula 6]

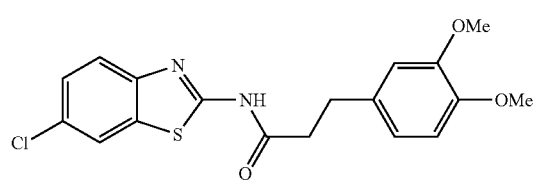

KY02111

[Formula 7]

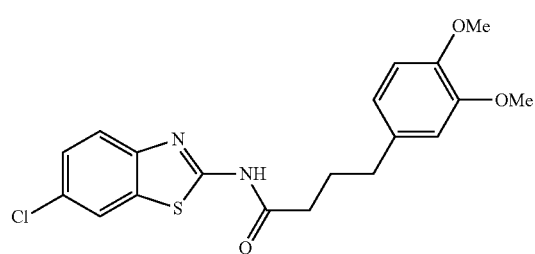

KY02114

[Formula 8]

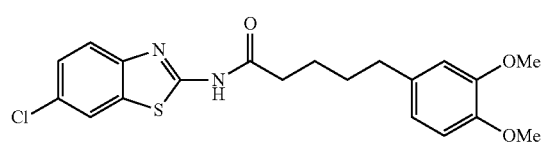

KY01045

[Formula 9]

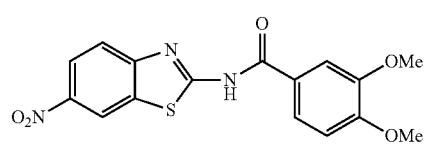

KY01040

[Formula 10]

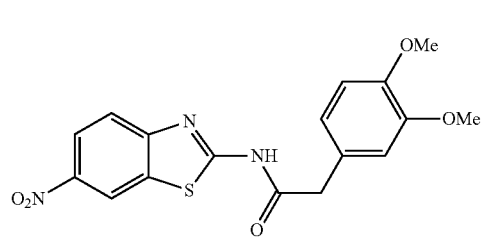

KY02109

[Formula 11]

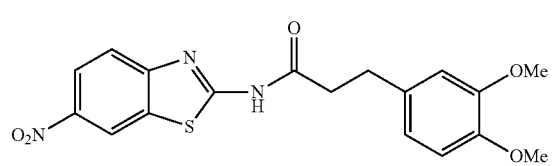

KY01042

-continued
[Formula 12]
KY01043
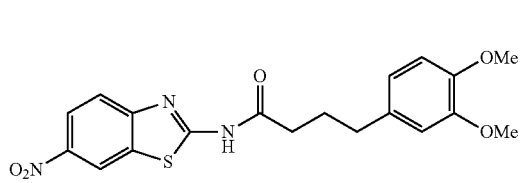
[Formula 13]
KY01046
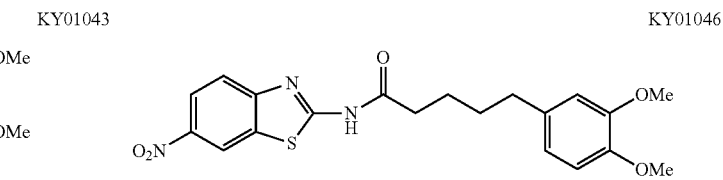
[Formula 14]
PB2852
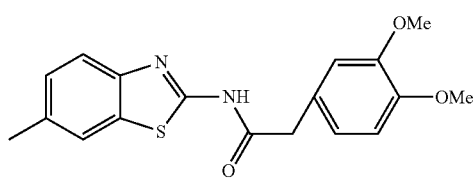
[Formula 15]
N11474
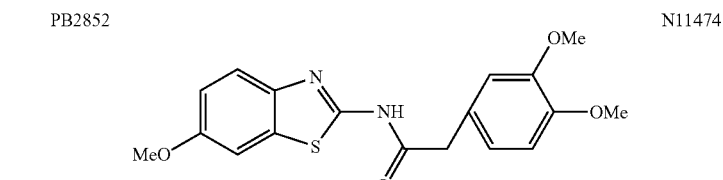
[Formula 16]
PB2572
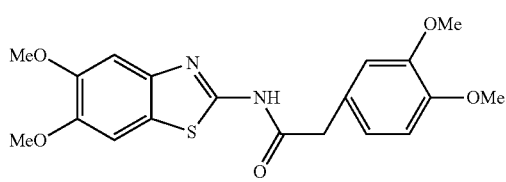
[Formula 17]
PB2570
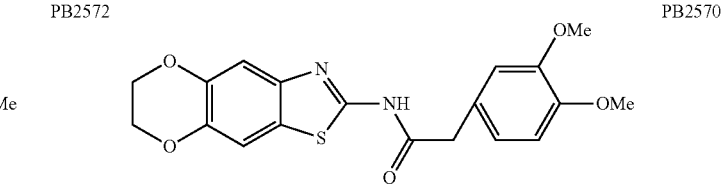
[Formula 18]
KY02104
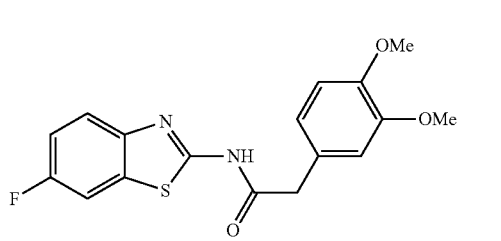
SO087
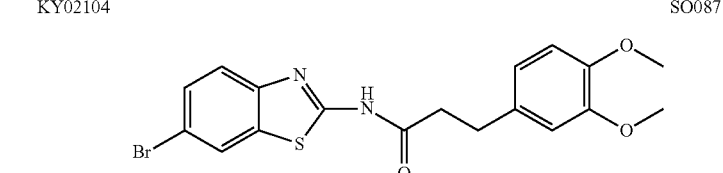
[Formula 19]
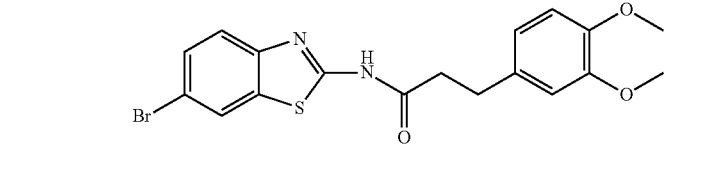
[Formula 20]
SO102
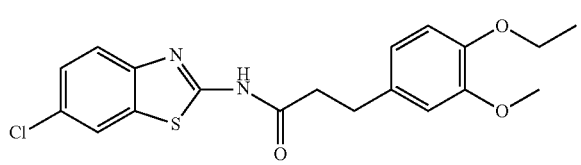
[Formula 21]
SO096
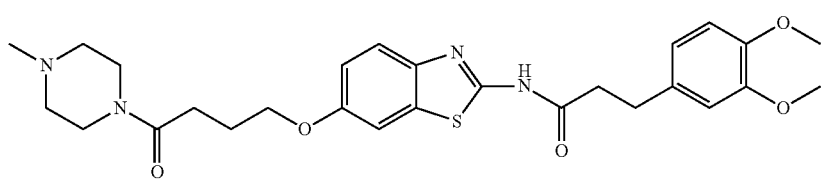
[Formula 22]
SO094
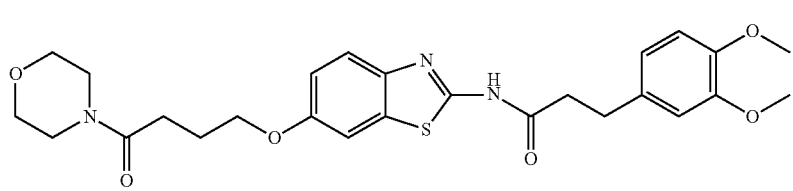

The compounds of the present invention are described in, for example, J. Med. Chem., 1965, 8 (5), pp 734-735 (incorporated herein by references) (N11474, T61164). Also, they are available from UkrOrgSynthesis Ltd. (PB2852, PB2572, and PB2570) and ENAMINE (T61164), etc.

The compounds of the present invention can be synthesized by the known method (J. Med. Chem., 1965, 8 (5), pp 734-735) (incorporated herein by references) or in accordance with the method described in Examples.

The term "pluripotent stem cells" herein used refers to cells having an ability to differentiate any type of cells constituting an adult body (pluripotency) and self-renewal capacity which is an ability to maintain the pluripotency during cell division. The "pluripotent stem cells" includes embryonic stem cells (ES cells), embryonic germ cells (EG cells), and induced pluripotent stem cell (iPS cells). The "pluripotent stem cells" may be cells of any species with no limitation, preferably mammalian cells, and more preferably rodent or primate cells. The present invention is particularly suitable for monkey or human pluripotent stem cells.

ES cells are pluripotent stem cells derived from early embryo and may be established from inner cell mass of a blastocyst or post-implantation epiblast in early embryo. Examples of ES cells include those described in the following references: human (Thomson J. A. et al., Science 282: 1145-1147 (1998), Biochem Biophys Res Commun. 345(3), 926-32 (2006); primates such as rhesus macaque and marmoset (Thomson J. A. et al., Proc. Natl. Acad. Sci. USA 92: 7844-7848 (1995); Thomson J. A. et al., Biol. Reprod. 55: 254-259 (1996)); rabbit (National Publication of International Patent Application No. 2000-508919); hamster (Doetshman T. et al., Dev. Biol. 127: 224-227 (1988)), hog (Evans M. J. et al., Theriogenology 33: 125128 (1990); Piedrahita J. A. et al., Theriogenology 34: 879-891 (1990); Notarianni E. et al., J. Reprod. Fert. 40: 51-56 (1990); Talbot N. C. et al., Cell. Dev. Biol. 29A: 546-554 (1993)), sheep (Notarianni E. et al., J. Reprod. Fert. Suppl. 43: 255-260 (1991)), cow (Evans M. J. et al., Theriogenology 33: 125-128 (1990); Saito S. et al., Roux. Arch. Dev. Biol. 201: 134-141 (1992)), and mink (Sukoyan M. A. et al., Mol. Reorod. Dev. 33: 418-431 (1993)) (these references are herein incorporated by reference).

EG cells are pluripotent stem cells derived from primordial germ cells, and examples include human EG cells (Shamblott, et al., Proc. Natl. Acad. Sci USA 95: 13726-13731 (1998)) (the reference is herein incorporated by reference.).

The term "iPS cells" herein used refers to pluripotent stem cells induced from cells other than pluripotent stem cells such as somatic cells and tissue stem cells. Methods for preparing iPS cells are described in the following references, for example: WO2007/069666, WO2009/006930, WO2009/006997, WO2009/007852, WO2008/11.8820, Cell Stem Cell 3(5): 568-574 (2008), Cell Stem Cell 4(5): 381-384 (2009), Nature 454: 646-650 (2008), Cell 136(3): 411-419 (2009), Nature Biotechnology 26: 1269-1275 (2008), Cell Stem Cell 3: 475-479 (2008), Nature Cell Biology 11: 197-203 (2009), Cell 133(2): 250-264 (2008), Cell 131(5): 861-72 (2007), Science 318 (5858): 1917-20 (2007) (those references are herein incorporated by reference.). However, cells prepared by any method as long as they are pluripotent stem cells induced artificially are included in the "iPS cells" of the present invention.

The composition of the present invention may be added to a differentiation medium for cardiac muscle cells of pluripotent stem cells at a final concentration of the active ingredient of, for example, 0.5 to 20 μM. The differentiation medium for cardiac muscle cell may be any conventional medium used for cardiac muscle cell differentiation of pluripotent stem cells and the composition of the differentiation medium is not specifically limited. Examples of the differentiation medium include the IMDM-based differentiation medium for cardiac muscle cells (having the composition described below and used in the examples), DMEM-based differentiation medium for cardiac muscle cells (200 ml DMEM/F12 medium (Sigma) containing 50 ml bovine fetal serum (GIBCO), 2.5 ml MEM non-essential amino acid solution (Sigma), 2.5 ml penicillin-streptomycin (GIBCO), 200 mM L-glutamine, and 2.5 ml 2-mercaptoethanol), and StemPro-34SFM (GIBCO)+BMP4 (10 ng/ml). It is not necessary to use feeder cells such as END2 cells when the composition of the present invention is used. The composition of the present invention may be added at an appropriate time depending on the type of pluripotent stem cells and composition of the differentiation medium for cardiac muscle cell to be used. When monkey or human ES cells are cultured in the IMDM-based differentiation medium for cardiac muscle cells used in the examples, the composition of the present invention may be added to the differentiation medium for cardiac muscle cells during day 6 to 14 of culture.

The composition of the present invention may be used in combination with a different cardiac muscle cell differentiation promoter(s) such as nitrovin, cytokines (combination of bFGF, BMP4, VEGF, DKK1 and Activin A), or Wnt signaling inhibitors. The "cardiac muscle cell differentiation promoter" in the present invention include various substances effective in promoting cardiac muscle cell differentiation and thus, in this sense, the composition of the present invention is also one of the "cardiac muscle cell differentiation promoter". The "Wnt signaling inhibitor" in the present invention refers to a substance which inhibits the Writ signaling pathway and examples include known compounds such as TWP2, XAV939, and IWR1, and proteins such as G-CSF, IGFBP4, and Dkk1. The composition of the present invention is also a useful "Wnt signaling inhibitor" in the present invention. More specifically, the embodiment, in which the composition of the present invention and a Wnt signaling inhibitor are used in combination, includes embodiments in which different types of the composition of the present invention are used. Preferably, the different cardiac muscle cell differentiation promoters used in combination are those having different action mechanism from the composition of the present invention, and examples of such promoters include IWP2 and XAV939. The administration schedule of the different cardiac muscle cell differentiation promoter may be determined as appropriate by those skilled in the art, depending on the agent to be used.

The present invention also provides a kit for promoting cardiac muscle cell differentiation containing the composition of the present invention. The kit of the present invention may contain a different cardiac muscle cell differentiation promoter(s) in addition to the composition of the present invention. The composition of the present invention and the different cardiac muscle cell differentiation promoter may be kept in separate containers or in a same container.

The present invention also provides a method for inducing cardiac muscle cell differentiation and a method for preparing cardiac muscle cells. The methods of the present invention are characterized in that pluripotent stem cells are cultured in a medium containing the composition of the present invention. In an embodiment, the method of the present invention comprises culturing pluripotent stem cells in a differentiation medium for cardiac muscle cells, adding the composition of the present invention to the differentiation medium such that the final concentration of the active ingredient is 0.5 to 20 μM during day 6 to 14 of culture and confirming differentiation of the pluripotent stem cells into cardiac muscle cells at day 18 of culture. Differentiation into cardiac muscle cells may be detected from the number of beating colonies of cardiac muscle cells or expression level of a marker of cardiac muscle cell differentiation such as α-MHC gene.

In the methods of the present invention, a different cardiac muscle cell differentiation promoter(s), in addition to the composition of the present invention, may further be added to a medium.

The cardiac muscle cells prepared by the method of the present invention may be used for evaluation of drug safety in vitro or as cardiac muscle cells as transplant to treat heart diseases.

The present invention also provides a compound having Formula (I):

[Formula 23]

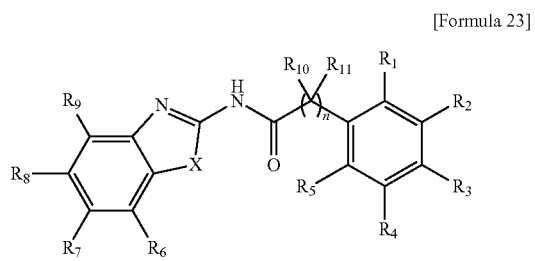

wherein $R_1$, $R_4$ and $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom, $R_2$ and $R_3$ are a linear or a branched alkoxy group having 1 to 5 carbon atoms, or $R_2$ and $R_3$ join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is an oxygen atom; a sulfur atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, with the proviso that when n is 1 or 2, $R_7$ is not Cl nor a methoxy group, $R_2$ is not a methoxy group, or a salt thereof.

In a preferred embodiment, $R_1$, $R_4$ and $R_5$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, preferably a hydrogen atom.

In a preferred embodiment, $R_2$ and $R_3$ are a methoxy group, an ethoxy group or a propoxy group.

In a preferred embodiment, $R_6$ and $R_9$ are each independently a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, preferably a hydrogen atom.

In a preferred embodiment, $R_7$ is a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom; or $R_7$ and $R_8$ join together to form —O—$CH_2$—O— or —O—$(CH_2)_2$—O—.

In an embodiment, $R_7$ is a linear alkoxy group having 1 to 5 carbon atoms which is substituted with a group —C(O)A, and the group —C(O)A binds to the terminal carbon atom of the alkoxy group.

In a preferred embodiment, A contains at least one nitrogen atom and examples of such an A include a pyrrolidinyl, imidazolidinyl, pyrazolidinyl, pyrrolyl, imidazolyl, pyrazolyl, thiazolyl, isothiazolyl, oxazolyl, isooxazolyl, piperidinyl, piperazinyl, morpholinyl, pyridyl, pyrimidinyl, pyrazinyl and pyridazinyl group which are unsubstituted or substituted with a linear or branched alkyl group having 1 to 5 carbon atoms. In a more preferred embodiment, A is a piperidinyl group, a piperazinyl group or a morpholinyl group which is unsubstituted or substituted with a linear or branched alkyl group having 1 to 5 carbon atoms. In a further preferred embodiment, A is a piperidin-1-yl group, a piperazin-1-yl group or a morpholin-4-yl group which is unsubstituted or substituted with a linear or branched alkyl group having 1 to 5 carbon atoms.

In a preferred embodiment, $R_{10}$ and $R_{11}$ are a hydrogen atom.

In a preferred embodiment, X is a sulfur atom.

In a preferred embodiment, n is an integer of 0 to 4. In another preferred embodiment, n is an integer of 1 to 6, an integer of 1 to 4, or 2 or 3.

In a preferred embodiment, the compounds of the present invention are

[Formula 24]

KY02114

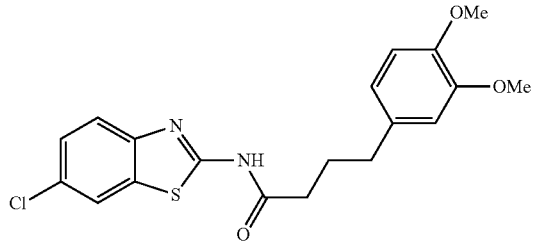

[Formula 25]

SO087

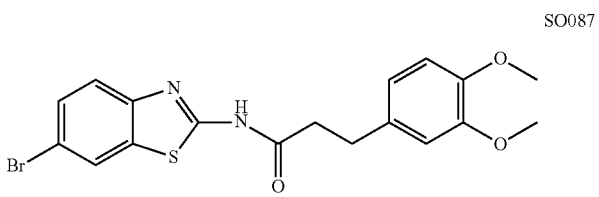

[Formula 26]

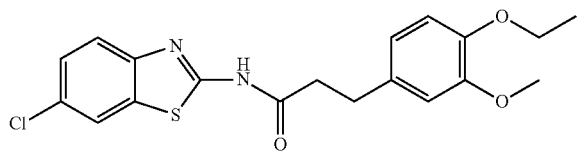

SO102

[Formula 27]

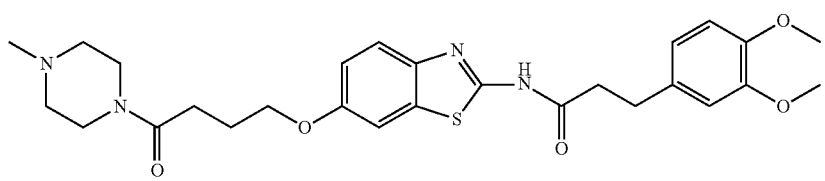

SO096

[Formula 28]

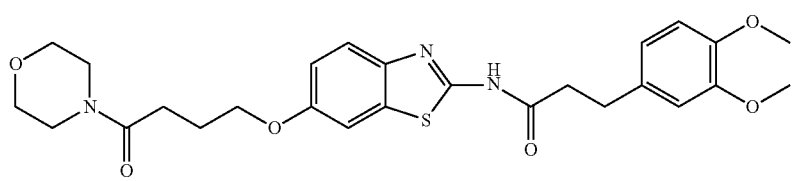

SO094

The present invention is described further in detail with reference to the following examples.

EXAMPLE (1) Screening of Library Compounds

Figure 2:
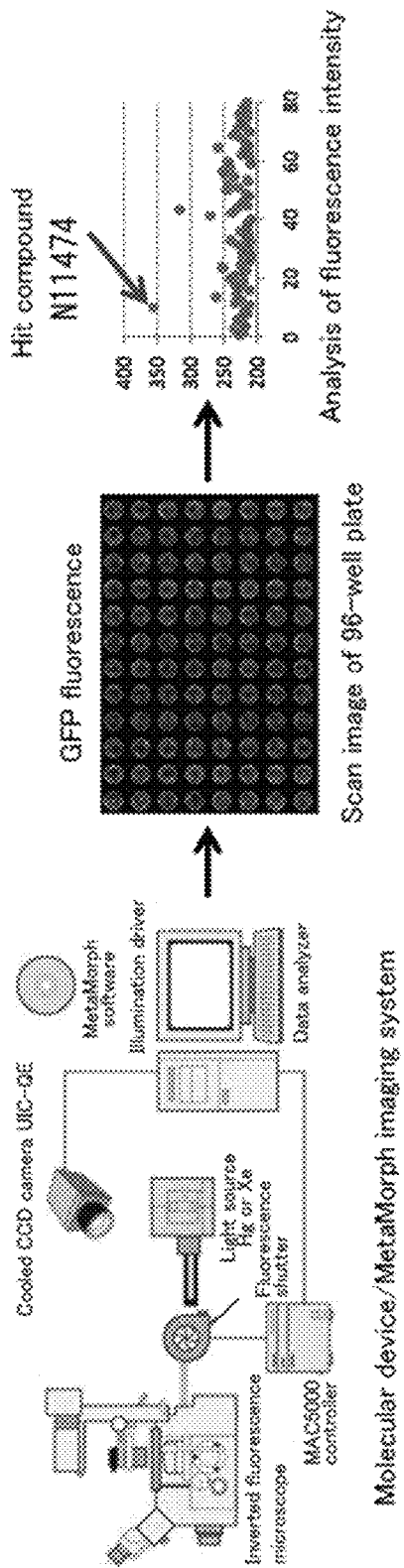
FIG. 2 illustrates a screening system and detection of N11474.

As described in FIG. 1, screening of agents which promote cardiac muscle cell differentiation of monkey ES cells was performed. A vector expressing green fluorescent protein (GFP) under control of promoter of α-MHC gene, a marker of cardiac muscle cell differentiation, was introduced into monkey ES cell line (CMK 6.4 cynomolgus monkey ES cells) and the cells were seeded on 96-well culture plates (Greiner/655090: 96 well FIA black plate) in $5.0 \times 10^3$ cells/well, and cultured for 14 days in an IMDM-based differentiation medium for cardiac muscle cells (200 ml. IMDM (Sigma 13390) containing 50 ml bovine fetal serum (GIBCO 10099-141), 2.5 ml MEM non-essential amino acid solution (Sigma M7145), 2.5 ml penicillin-streptomycin (GIBCO 15140), 2.5 ml 200 mM L-glutamine, 2 μl 2-mercaptoethanol (Sigma M7522), 255 μl 5N NaOH). During day 6 to 14 of culture, 9,600 library compounds were added into separate wells (about 1 to 5 μM compound/well). Then, at day 1.4 of culture, GFP expression level was determined by using HCS (high contents screening) system (Molecular device/MetaMorph imaging system). As a result, the wells to which the low-molecular compound N11474 was added indicated high GFP expression levels, and N11474 was revealed to be effective in promoting cardiac muscle cell differentiation (FIG. 2).

(2) Structure-Activity Relationship of KY02111 and Analogous Compounds Thereof

Figure 3:
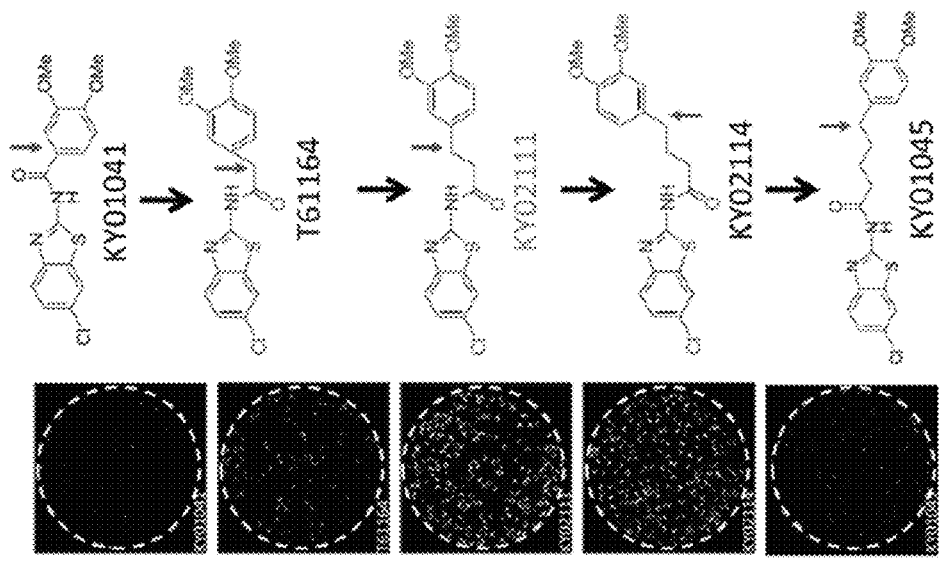
FIG. 3 illustrates the structure-activity relationship of KY02111 and analogous compounds thereof.
Figure 3:
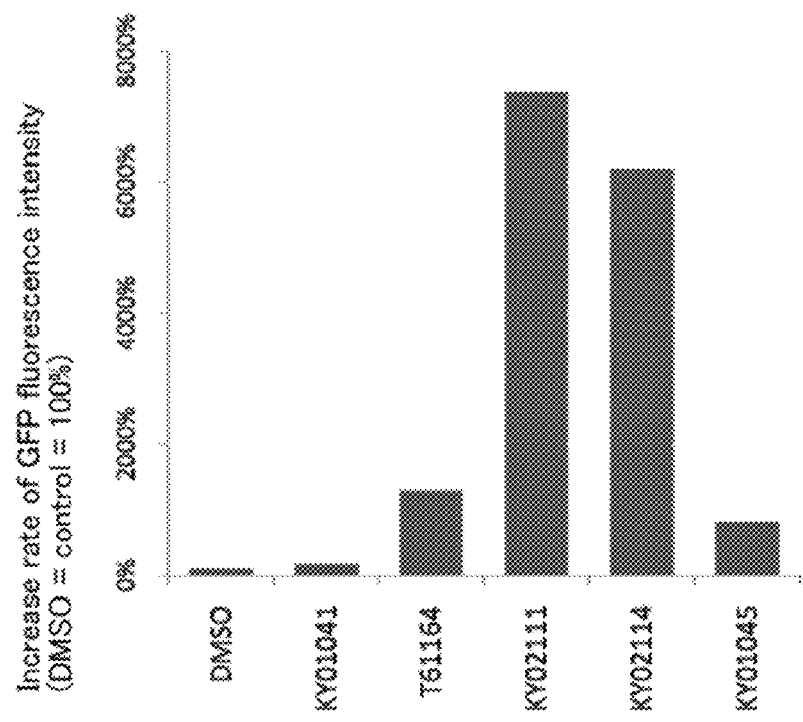

KY02111, an analog of N11474 which was revealed to be effective in promoting cardiac muscle cell differentiation and analogous compounds thereof were synthesized and examined for the effect of promoting cardiac muscle cell differentiation. Monkey ES cells were seeded on a 6-well culture plate (Asahi Glass/5816-006: Ezview culture plate) in $4.0 \times 10^5$ cells/well, each compound was added thereto such that the final concentration thereof was 10 μM during day 4 to 10 of culture, and the GFP expression was observed at day 14 of culture. As a result, significant increases in the GFP expression level were found in accordance with the molecular structure of the compounds (FIG. 3). Also, the effect of promoting cardiac muscle cell differentiation was suggested to correlate with the length of a carbon chain binding to the dimethoxyphenyl group (FIG. 3).

(3) Comparison of Nitrovin and Cytokines

Figure 4:
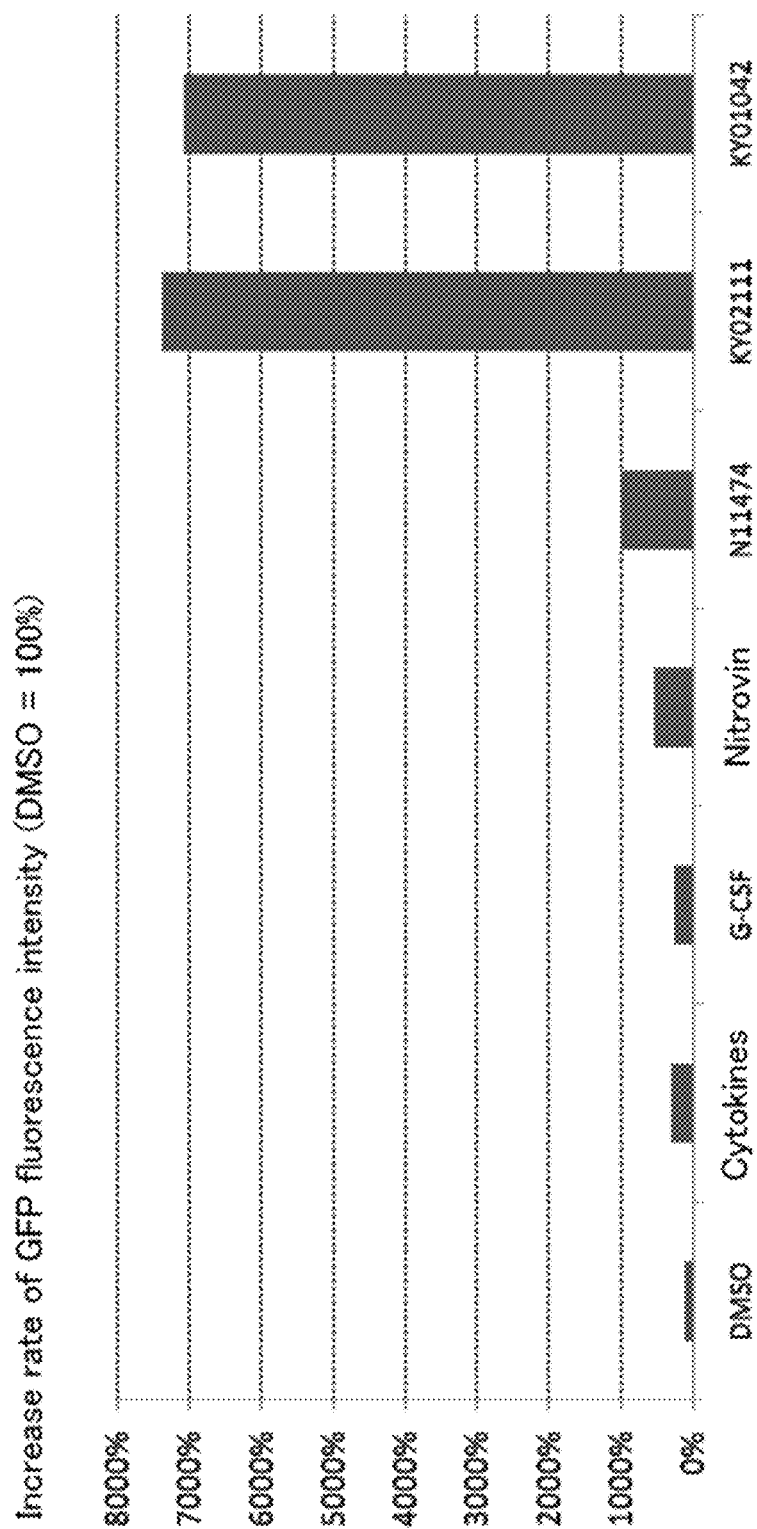
FIG. 4 illustrates the comparison in the effects of promoting cardiac muscle cell differentiation among cytokines, G-CSF, nitrovin, N11474, KY02111 and KY01042.

Cytokines (bFGF, BMP4, VEGF, DKK1, Activin A) known as a cardiac muscle cell differentiation promoter, granulocyte-colony stimulating factor (G-CSF), and nitrovin which was found effective in promoting cardiac muscle cell differentiation by the present inventors were compared with the compounds of the present invention in terms of the effect of promoting cardiac muscle cell differentiation based on the increase of GFP expression level. In the same manner as in the above (2), monkey ES cells were seeded on a 6-well plate, N11474, KY02111, KY01042 (final concentration 10 μM each) and G-CSF (final concentration 5 ng/ml) were added during day 4 to 10 of culture, nitrovin (final concentration 5 μM) was added during day 8 to 14 of culture, and cytokines (bFGF, BMP4, VEGF, DKK1, Activin A) (at respective final concentrations 5 ng/ml, 10 ng/ml, 10 ng/ml, 150 ng/ml and 3 ng/ml) were added during day 1 to 14 of culture, and the GFP expression was observed at day 14 of culture. As a result, N11474, KY02111 and KY01042 showed far higher increases (N11474=1000%, KY02111=7400% and KY01042=7000%) in the GFP expression level than cytokines (about 300%), G-CSF (about 250%) and nitrovin (about 400%) (FIG. 4).

(4) Synergistic Effect with Nitrovin

Figures 1, 5:
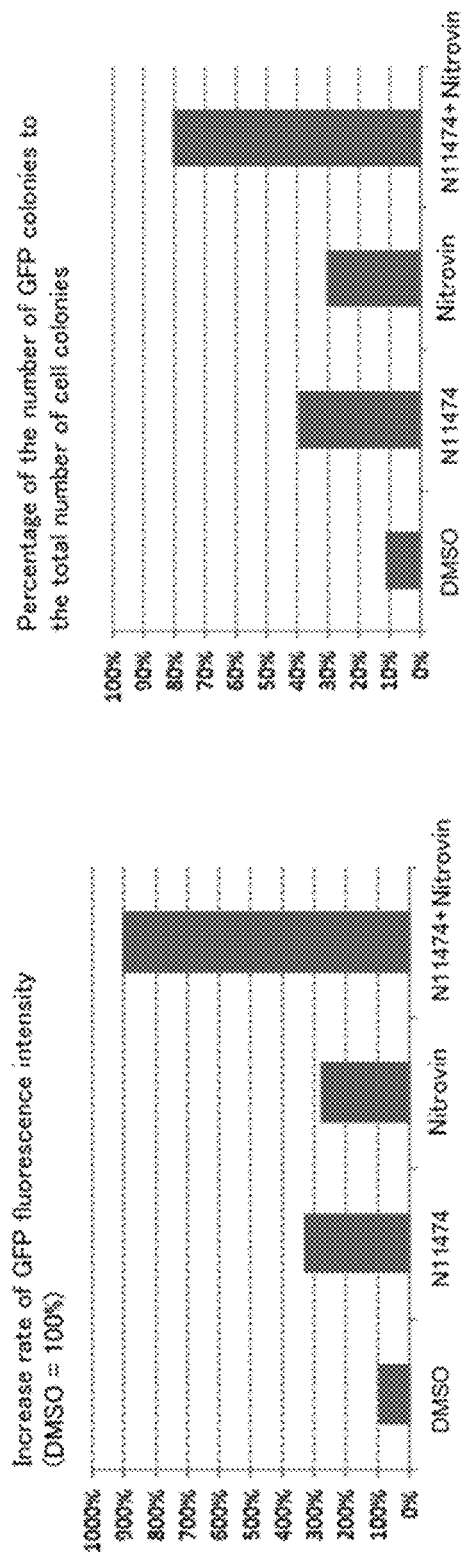
Figure 5:
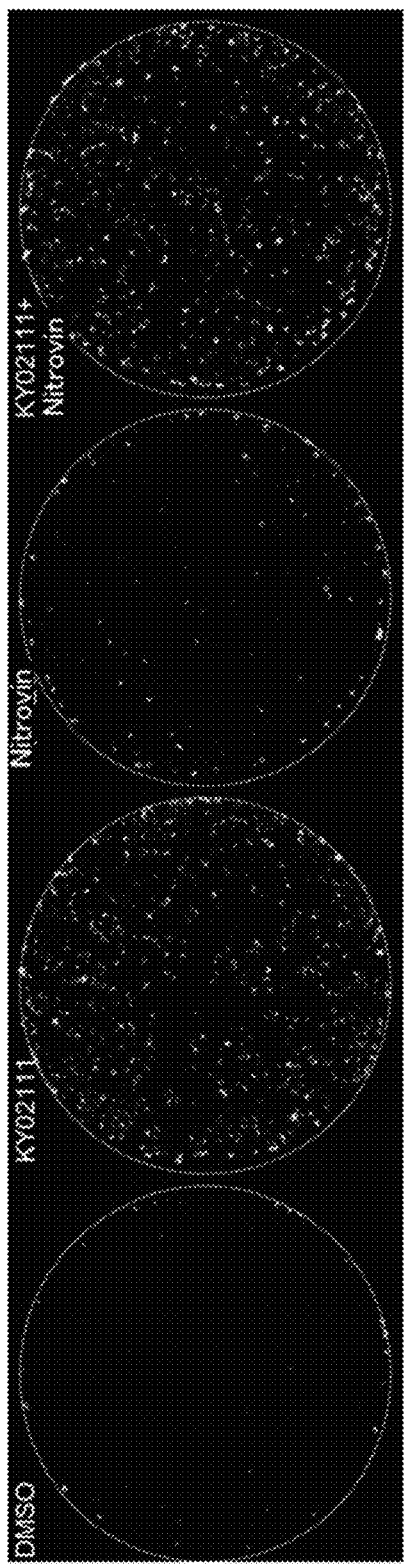
Figure 2:
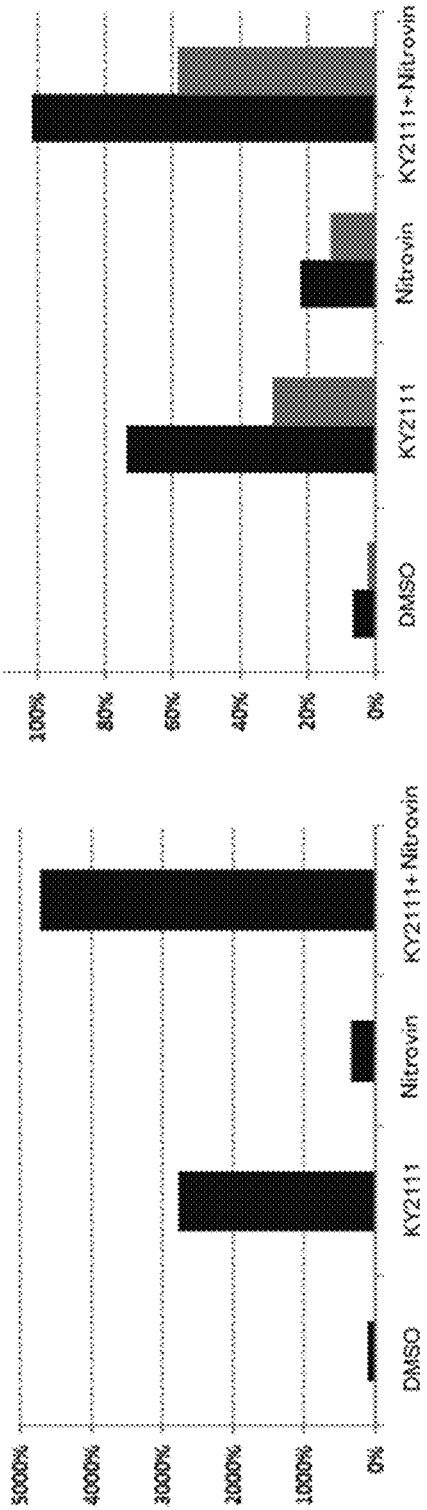

Nitrovin and N11474 were examined for the synergistic effect in the effect of promoting cardiac muscle cell differentiation. N11474 (10 μM) was added during day 4 to 10 of culture and nitrovin (3 μM) was added during day 8 to 14 of culture, and the GFP expression was observed at day 14 of culture. As a result, the increase in the GFP expression level was about 3 to 4 times when nitrovin or N11474 was singly administered, whereas the level increased about 9 times when nitrovin and N11474 were used in combination (FIG. 5-1, left graph). Also, the proportion of the number of GFP colonies increased by an about 30 to 40% when nitrovin or N11474 was singly administered, whereas the proportion increased by about 80% when nitrovin and N11474 were used in combination (FIG. 5-1, right graph).

Similarly, nitrovin and KY02111 were examined for the synergistic effect in the effect of promoting cardiac muscle cell differentiation. KY02111 (5 μM) was added during day 4 to 8 of culture, nitrovin (1 μM) was added during day 8 to 12 of culture, and the GFP expression was observed at day 14 of culture. As a result, the increases in the GFP expression level were respectively about 3 times and about 30 times as much more than Control (DMSO) when nitrovin or KY02111 was singly administered, whereas the level increased about 50 times when nitrovin and KY02111 were used in combination (FIG. 5-2, left graph). Also, the ratios of number of GFP colonies increased respectively by about 22% and 73% when nitrovin or KY02111 was singly administered, whereas all the colonies were substantially (100%) GFP fluorescence positive when nitrovin and KY02111 were used in combination (FIG. 5-2, bottom right graph). Further, the proportions of beating colonies were about 16% and 30% respectively when nitrovin or KY02111 was singly administered, whereas the proportion was 58% when nitrovin and KY021.1 were used in combination (FIG. 5-2, bottom right graph).

(5) Effects of Promoting Differentiation of Monkey, Human And Mouse ES Cells into Cardiac Muscle Cells The effect of promoting differentiation of each of the ES/iPS cells into cardiac muscle cells were confirmed for N11474 and KY02111 with the GFP expression level and number of beating colonies used as the indicators. Human ES cell line (Kh-1 line) (Suemori, H., et al., Efficient establishment of human embryonic stem cell lines and long-term maintenance with stable karyotype by enzymatic bulk passage. Biochem Biophys Res Commun. 345(3), 926-32 (2006)) (incorporated herein by reference) was seeded in a 6-well plate (Asahi Glass/5816-006: Ezview culture plate) in 1.2×10^6 cells/well and cultured for 22 days, with BMP4 (10 ng/ml) added during day 0 to 4 of culture and N11474 (10 μM) or KY02111 (5 μM) added during day 4 to 14 of culture. Human iPS cell lines (253G1, IMR90-1, IMR90-4 and RCHIPC0003) (Takahashi, K., et al., Induction of pluripotent stem cells from adult human fibroblasts by defined factors. Cell. 131(5), 861-72 (2007); Yu, J., et al., Induced pluripotent stem cell lines derived from human somatic cells. Science. 318(5858), 1917-20 (2007)) (these references are herein incorporated by reference) were cultured for the cardiac muscle cell differentiation in the same manner as for the human ES cells. The cardiac muscle cells from mouse ES cells (R1) were differentiated in accordance with the method described in the reference (Transient inhibition of BMP signaling by Noggin induces cardiomyocyte differentiation of mouse embryonic stem cells. Yuasa S, Itabashi Y, Koshimizu U, Tanaka T, Sugimura K, Kinoshita M, Hattori F, Fukami S, Shimazaki T, Ogawa S, Okano H, Fukuda K. Nat. Biotechnol. 2005 May; 23(5): 607-11. Epub 2005 May 1. Erratum in: Nat. Biotechnol. 2005 July; 23(7):897.) (incorporated herein by reference). KY02111 (5 μM) was added for 3 days during day 6 to 9 of cardiac muscle cell differentiation culture and the beating colonies of cardiac muscle cells were analyzed at day 9. Monkey ES cells (CMK6.4) were cultured for cardiac muscle cell differentiation in the same manner as in the above (2).

Figure 6:
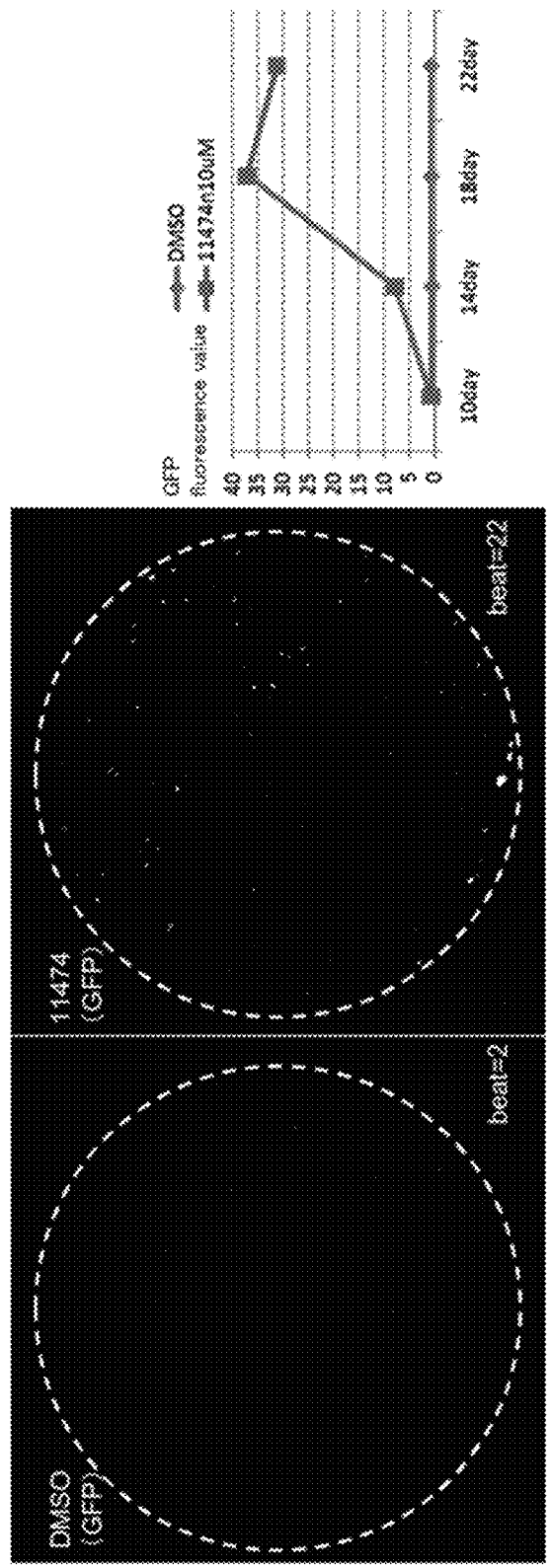
FIG. 6 illustrates the effect of N11474 on human ES cells in promoting cardiac muscle cell differentiation (increase of GFP expression level).

As a result, at day 14 and after of culture, a significant increase in the GFP expression level was observed (FIG. 6). Also, the number of beating colonies increased significantly with the maximum of about 60 times in monkey ES cells (CMK6.4), mouse ES cells (R1), human ES cells (Kh-1) and human iPS cells (253G1, IMR90-1, IMR90-4 and RCHIPC0003) by the administration of N11474 and KY02111 (Table 1). As described above, it was confirmed that these compounds were highly effective in promoting cardiac muscle cell differentiation for human ES and iPS cells and mouse ES cells.

TABLE 1

Effect of the compounds for promoting cardiac muscle cell differentiation (N11474, KY02111) on each ES/iPS cell line (Increase rate in the number of beating colonies as compared to the control (DMSO))

| ES/iPS cell line (line name) | Beating cardiac muscle cell differentiation efficiency (Control (DMSO) = 100%) |
| --- | --- |
| Monkey ES (CMK6.4) | 1850% (KY02111) |
| Human ES (Kh-1) | 1100% (N11474) |
| Mouse ES (R1) | 200% (KY02111) |
| Human iPS (253G1) | 1500% (KY02111) |
| Human iPS (IMR90-1) | 6100% (KY02111) |
| Human iPS (IMR90-4) | 4000% (N11474) |
| Human iPS (RCHIPC0003) | 1000% (KY02111) |

(6) Other Active Compounds (1)

Figures 1, 7:
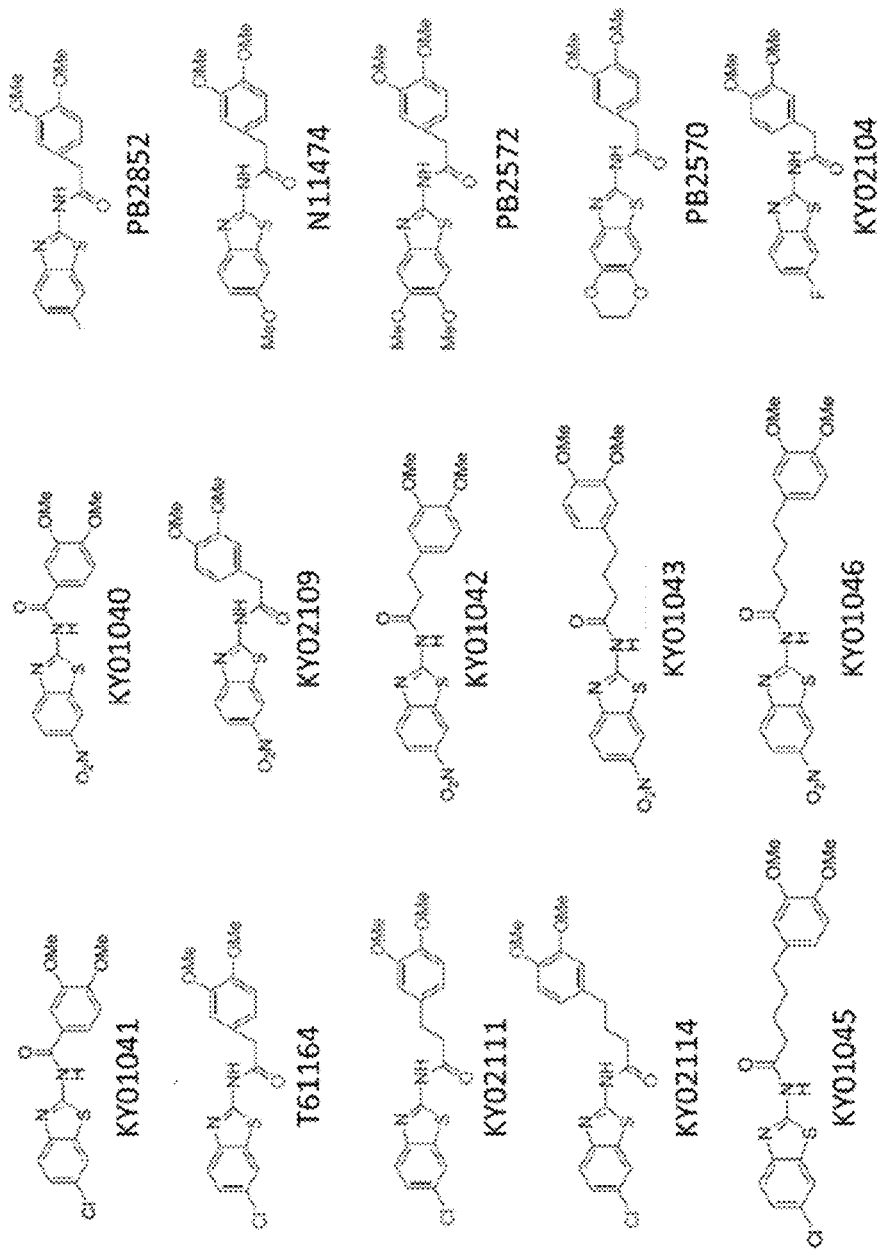
Figures 2, 7:
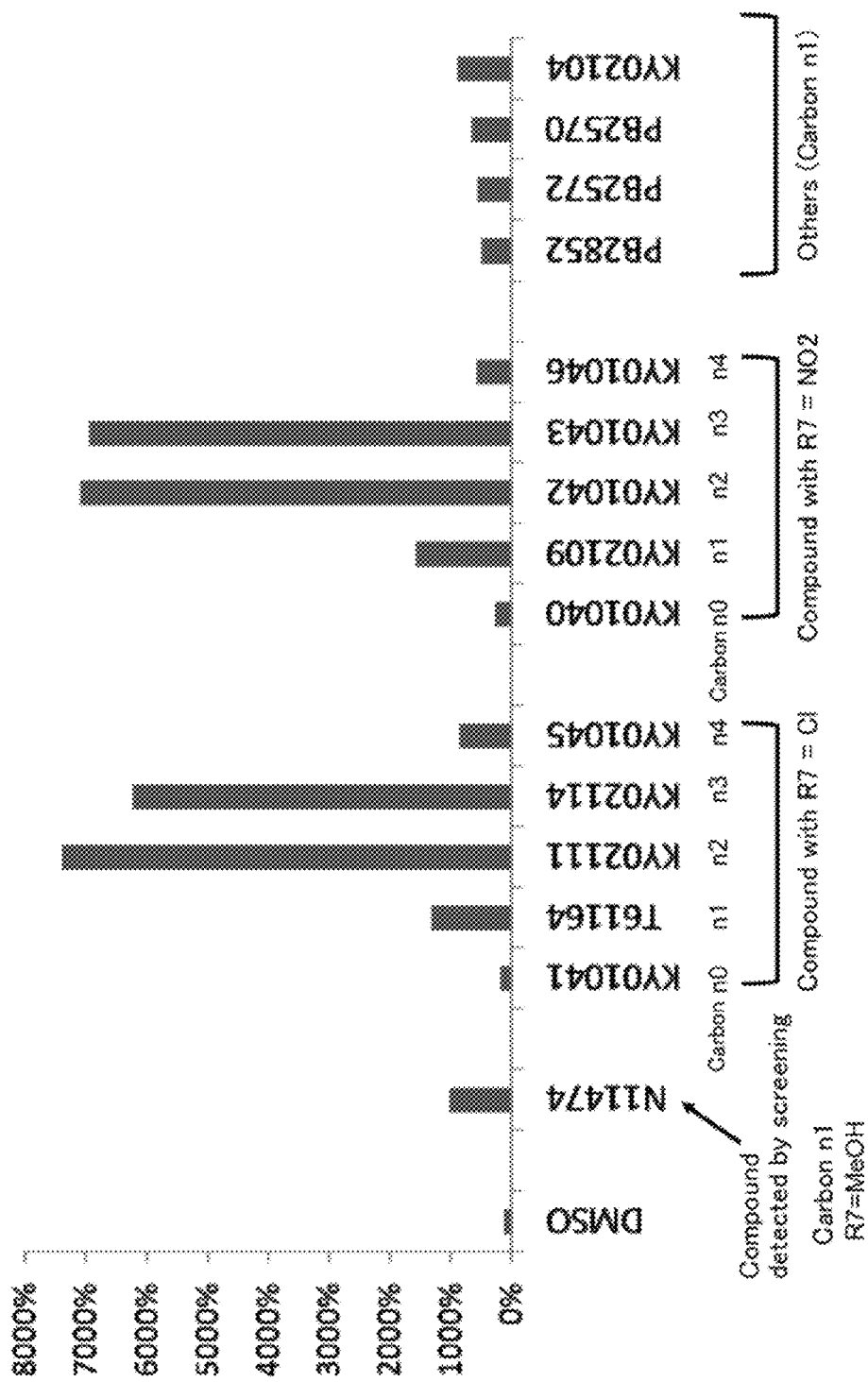

In the same manner as in the above (2), it was further found that some more analogous compounds were effective in promoting cardiac muscle cell differentiation (FIG. 7).

(7) Study on the Action Mechanism

Figure 8:
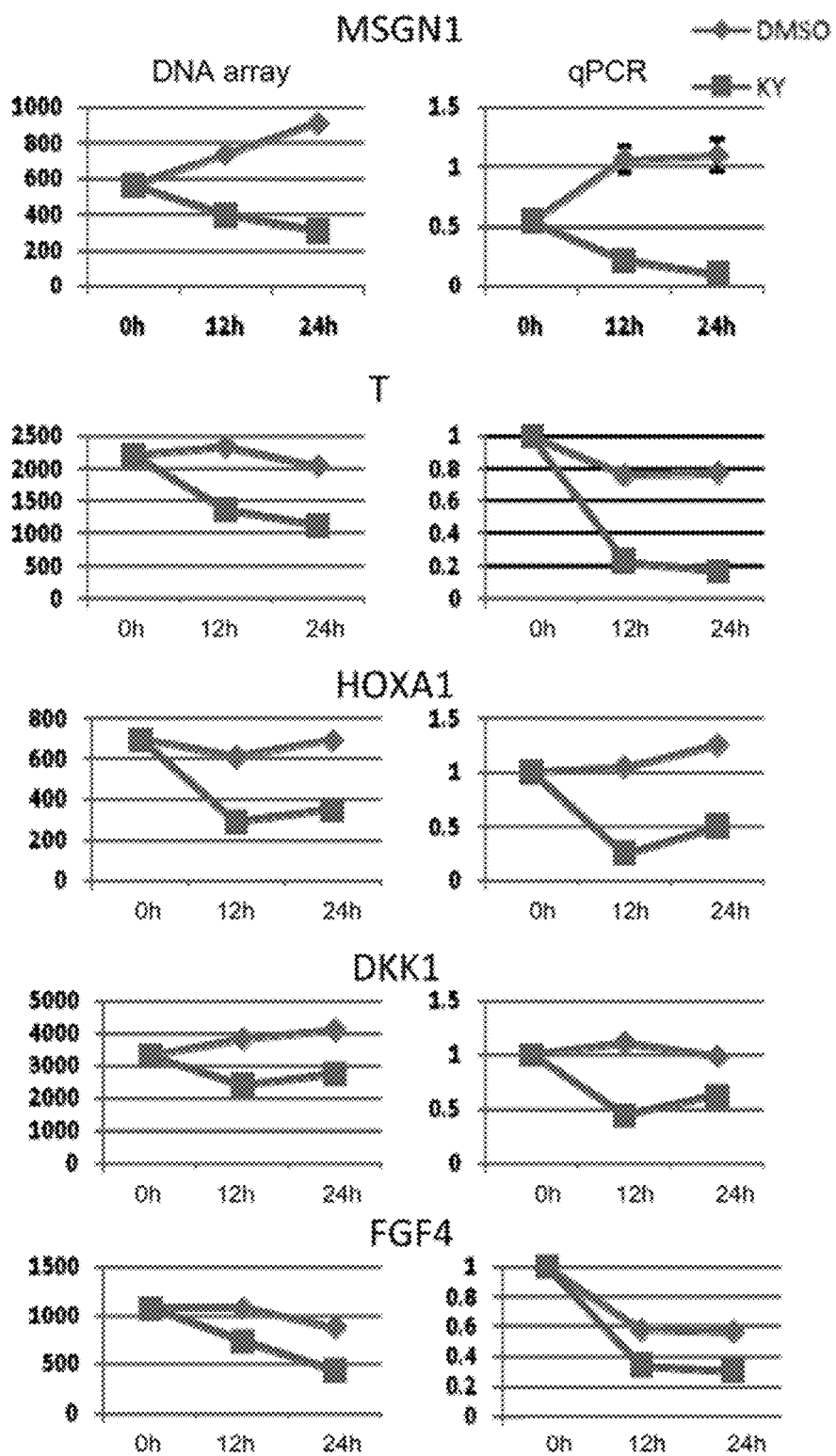
FIG. 8 illustrates the effect of KY02111 on gene expression.

To examine the action mechanism of compounds of the present invention, human iPS cells were seeded in the differentiation medium for cardiac muscle cells described in the above (1), DMSO or KY02111 (10 μM) was added at day 3 of culture and the gene expressions 12 hours and 24 hours after the addition were analyzed by the DNA array. As a result, it was revealed that expressions of the following genes were reduced by the addition of KY02111: (in the order of the genes whose expression were reduced most 12 hours later) HOXA1, MSGN1, NKD1, T, TNFRSF11B, DKK1, DKK4, CDX2, MSX1, NODAL, FGF4, PAPPA, PRRX1, LRAT, CYP1B1, SLC34A2, AXIN2, LGL1, SP5, MIXL1, APCDD1 and DSEL. The promoter analysis using the TCF/LEF transcription factor recognition sequence was performed and it was revealed that these genes contained many genes which function at the downstream of the Wnt signaling pathway. A part (MSGN1, HOXA1, T, Dkk1 and FGF4) of these genes was confirmed for the expression by the quantitative polymerase chain reaction (qPCR) and all of these genes had the same results as the DNA array analysis (FIG. 8).

Figures 1, 9:
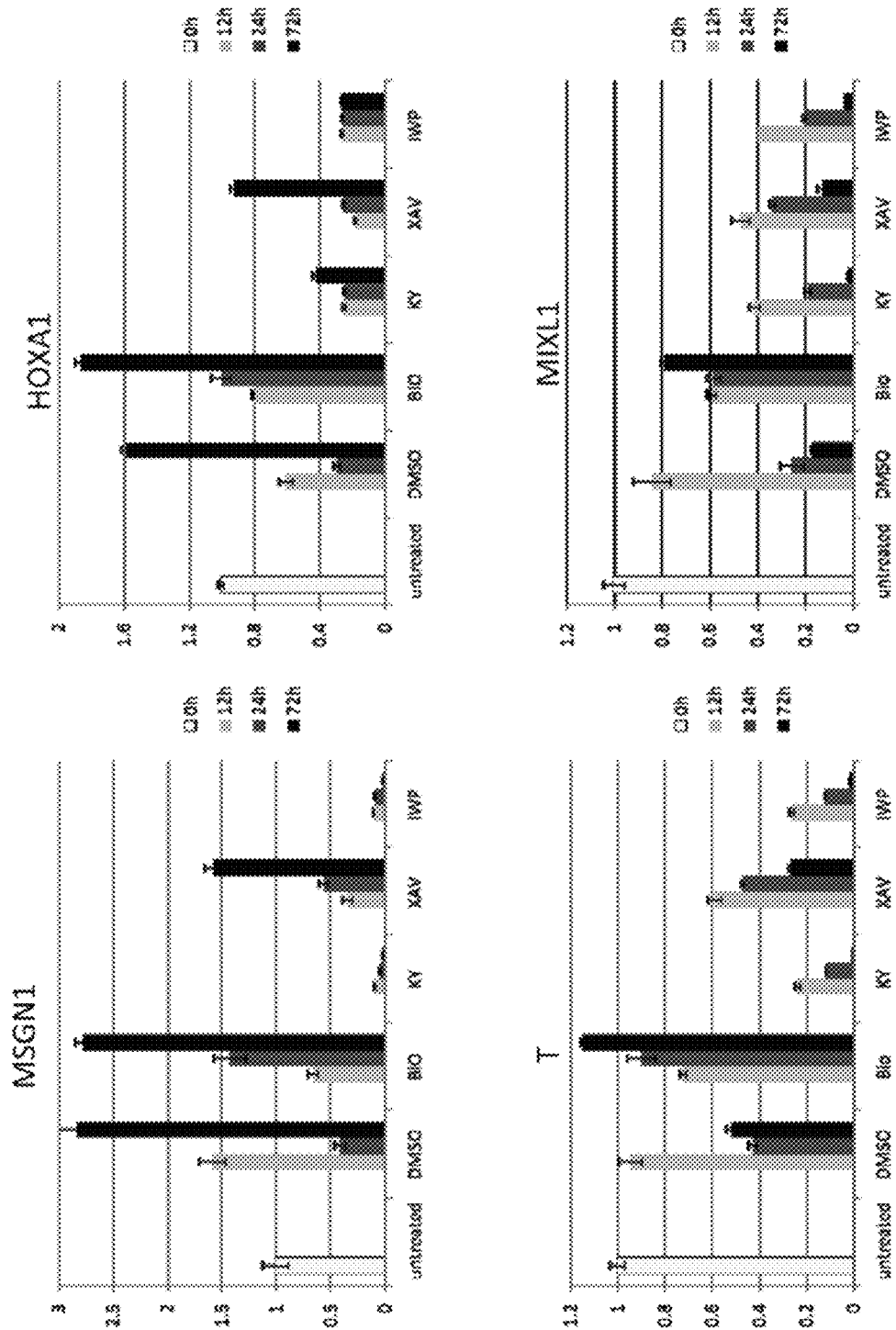
Figures 2, 9:
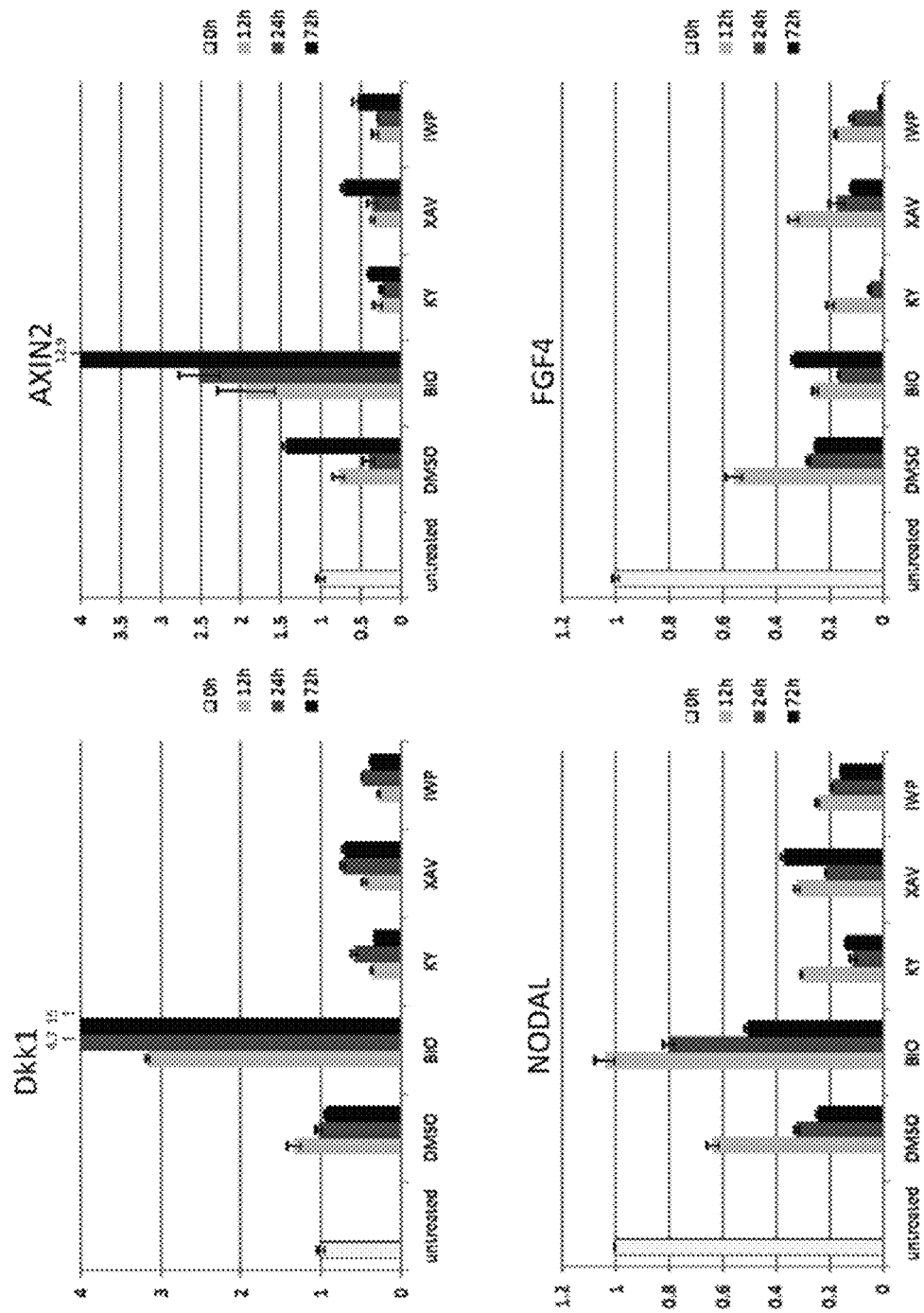

Next, the effects of KY02111, XAV939 and IWP-2, known Wnt signaling inhibitors, and BIO, a Wnt signaling activator, on the group of genes which were found to have reduced expression by the addition of KY02111 were analyzed by the quantitative polymerase chain reaction. The analyzed genes were as follows: MSGN1, HOXA1; T, MIXL1; Dkk1, AXIN2; NODAL and FGF4 (all known as Wnt signaling target genes). As a result, the expressions of these genes were also reduced by any of the compounds KY02111, XAV939 and IWP-2, whereas increased by BIO, the Wnt signaling activator (FIG. 9).

The above results suggest that the group of genes found to have reduced expression by the addition of KY02111 in the DNA array is the genes located at the downstream of the Writ signaling pathway and that KY02111 is a Wnt signaling inhibitor.

(8) Comparison in Effect of Promoting Cardiac Muscle Cell Differentiation

Figure 10:
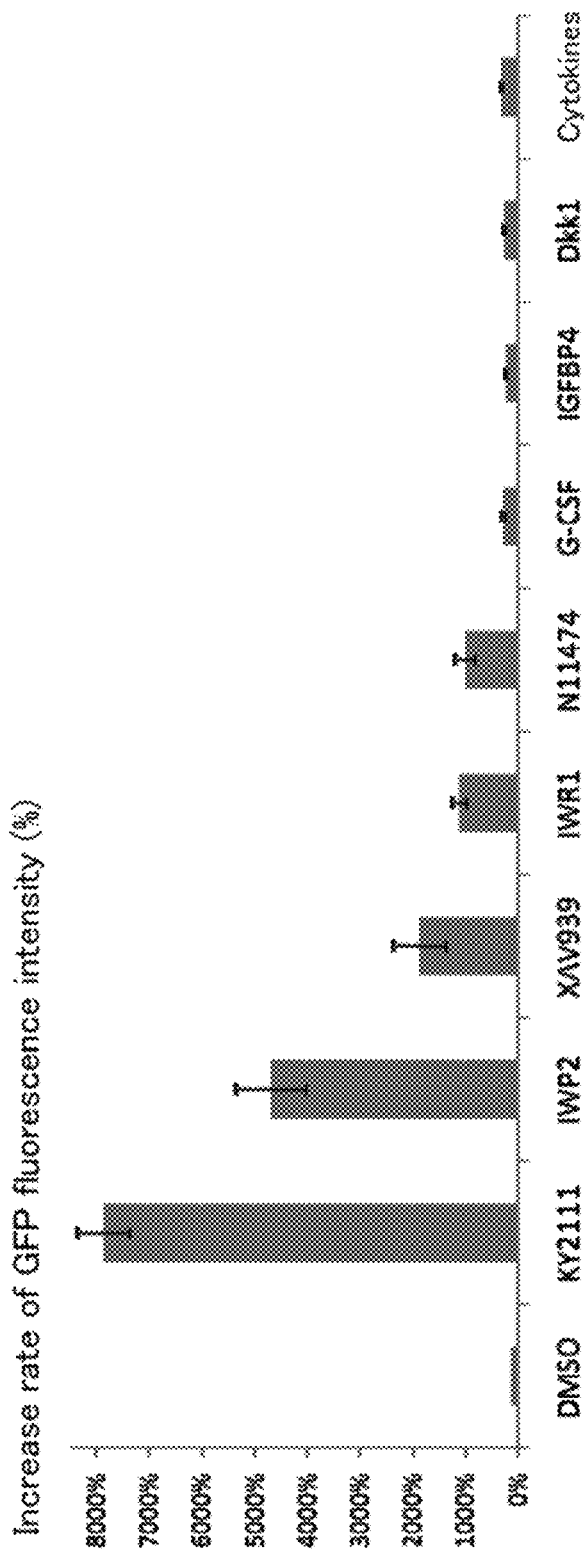
FIG. 10 illustrates the comparison in the effect of promoting cardiac muscle cell differentiation among KY02111, N11474, known Wnt signaling inhibitors (IWP2, XAV939, IWR1) and proteins (G-CSF, IGFBP4, Dkk1 and cytokines) known to have the effect of promoting cardiac muscle cell differentiation.

In the same manner as in the above (2), the effects of promoting cardiac muscle cell differentiation were compared among KY02111 and N11474, known Wnt signaling inhibitors (IWP2, XAV939 and IWR1), proteins known to be effective in promoting cardiac muscle cell differentiation (G-CSF, IGFBP4, Dkk1 and cytokines (a mixture of bFGF, BMP4, VEGF, DKK1 and Activin A)). Monkey ES cells were seeded on a 6-well plate, KY02111 and N11474 (final concentration 10 µM each), IWP2 (final concentration 10 µM), XAV939 (final concentration 10 µM), IWR1 (final concentration 10 µM), G-CSF (final concentration 5 ng/ml), IGFBP4 (final concentration 1 µg/ml) and Dkk1 (final concentration 150 ng/ml) were added during day 4 to 10 of culture and cytokines (a mixture of bFGF, BMP4, VEGF, DKK1 and Activin A) (at respective final concentrations 5 ng/ml, 10 ng/ml, 10 ng/ml, 150 ng/ml and 3 ng/ml) were added during day 1 to 14 of culture and the GFP expressions were observed at day 14 of culture. As a result, the known Wnt signaling inhibitors also showed the effect of promoting cardiac muscle cell differentiation but KY02111 had the strongest effect of promoting cardiac muscle cell differentiation (FIG. 10).

Figure 11:
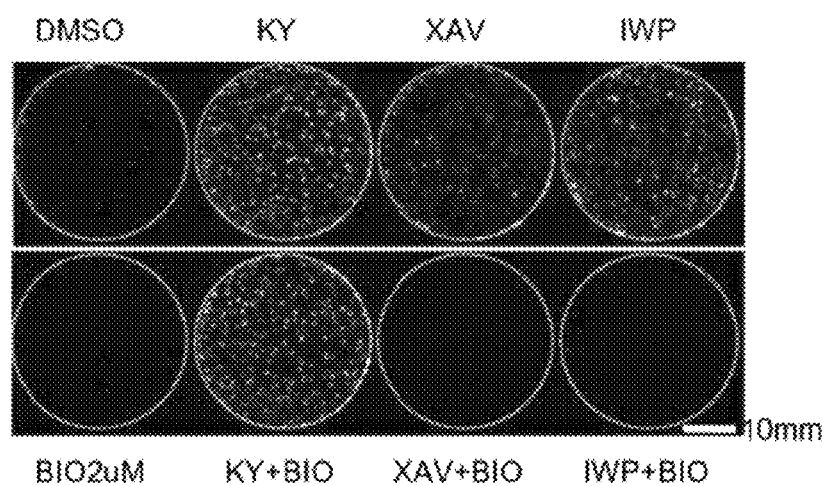
Figure 1:
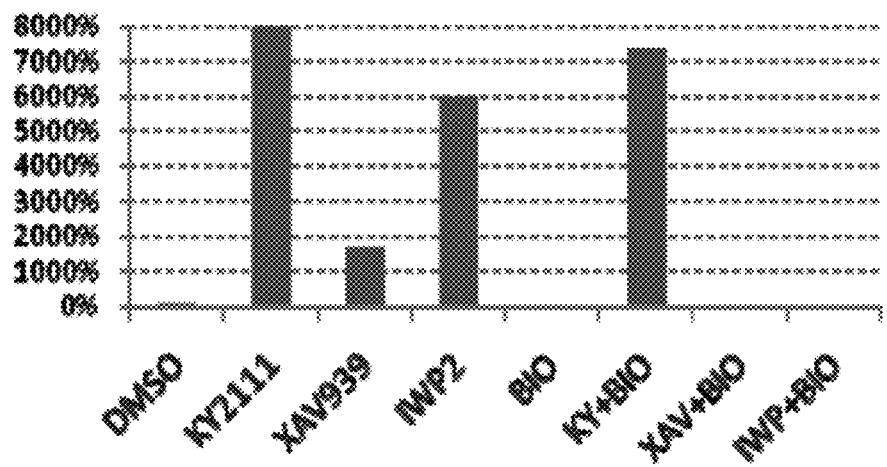
Figures 2, 11:
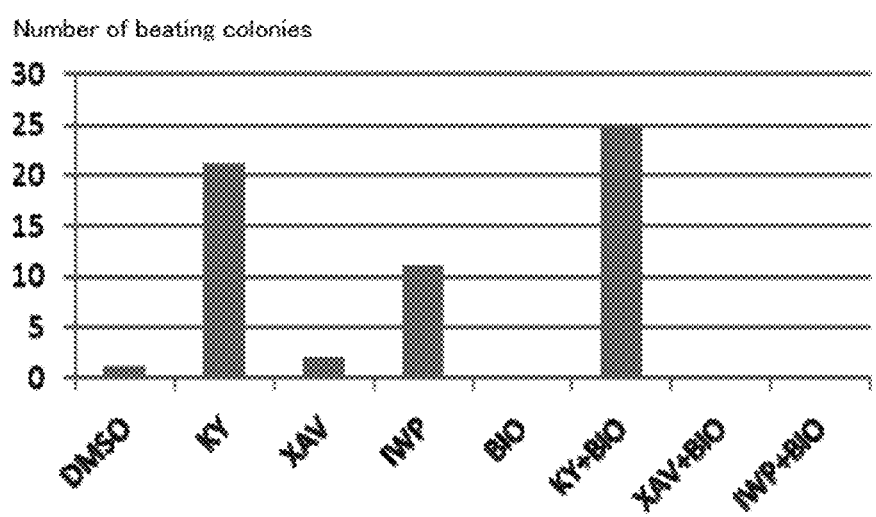

(9) Effect of a Wnt Signaling Activator on the Effect of Promoting Cardiac Muscle Cell Differentiation The effect of BIO, a Wnt signaling activator, on the effect of promoting cardiac muscle cell differentiation of KY02111, XAV939 and IWP2 was analyzed. In the same manner as in the above (8), BIO (final concentration 5 µM) was added to the monkey ES cells together with KY02111, XAV939 or IWP2 during day 4 to 10 of culture, and the GFP expression was observed at day 14 of culture. As a result, BIO inhibited the effect of cardiac muscle cell differentiation by XAV939 and IWP2 but did not inhibit the effect by KY02111 (FIG. 11). The same results were found when the number of beating colonies was analyzed using human iPS cells (IMR90-1) as described in the above (5) (FIG. 11). These results suggest that KY02111 has the different action mechanism of the cardiac muscle cell differentiation effect from the known Wnt signaling inhibitors.

(10) Synergistic Effect with Known Wnt Signaling Inhibitors

Figure 12:
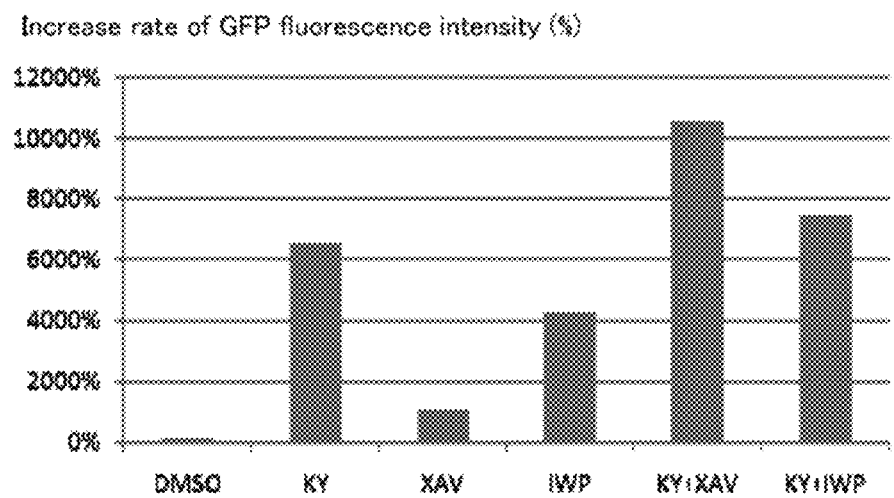
FIG. 12 illustrates the synergistic effect between KY02111 and XAV939 or IWP2 in promoting cardiac muscle cell differentiation.
Figure 12:
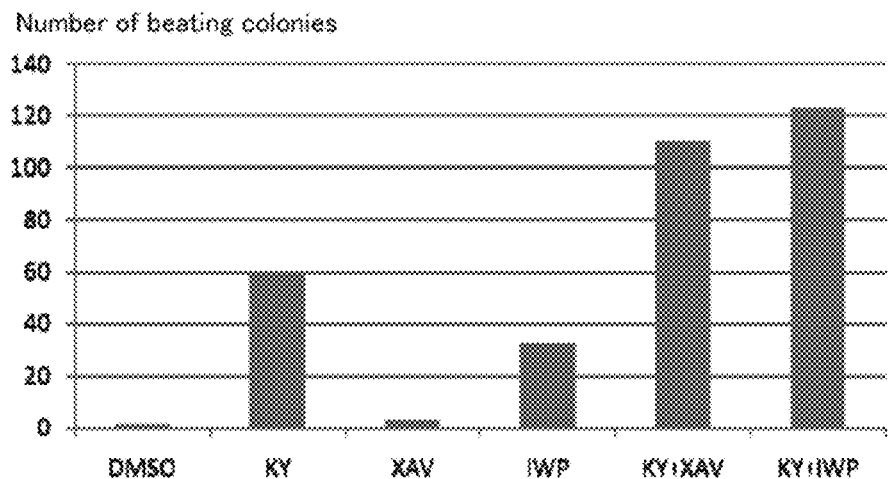

The synergistic effects between KY02111 and a known Wnt signaling inhibitor XAV939 or IWP2 in the promotion of cardiac muscle cell differentiation were analyzed. In the same manner as in the above (8), KY02111, XAV939 and IWP2 were added to monkey ES cells during day 4 to 10 of culture, and the GFP expression was observed at day 14 of culture. As a result, the synergistic effect was observed between KY02111 and XAV939 (FIG. 12). Also, the number of beating colonies was analyzed using human iPS cells (IMR90-1) as described in the above (8), and the synergistic effects were observed between KY02111 and XAV939 and KY02111 and TWP2 (FIG. 12-2). The above results suggest that KY02111 has a different action mechanism from the known Wnt signaling inhibitors and an even stronger effect of promoting cardiac muscle cell differentiation is achieved when both are used in combination.

(11) Other Active Compounds (2)

Figure 13:
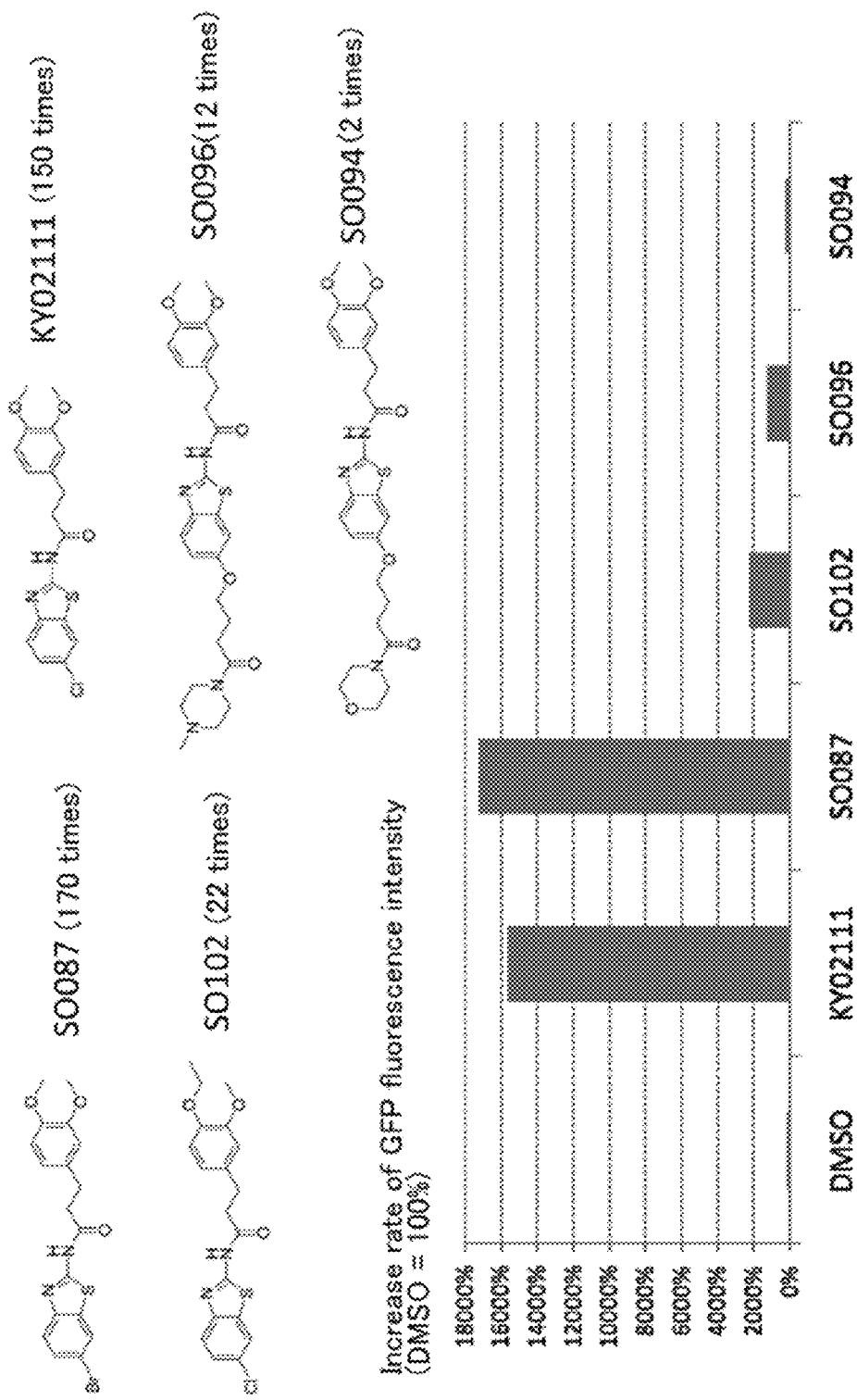
FIG. 13 illustrates compounds which are effective in promoting cardiac muscle cell differentiation (2) and the effect of promoting cardiac muscle cell differentiation of each of the compounds.

In the same manner as in the above (2), some more compounds were further found to be effective in promoting cardiac muscle cell differentiation (FIG. 13).

(12) Preparation Examples of the Compounds of the Present Invention

KY01041

3,4-Dimethoxybenzoylyl chloride (100 mg, 0.55 mmol) and triethylamine (83.0 µl, 6 mmol) were dissolved in methylene chloride (500 µl), 2-amino-6-chlorobenzothiazole (105 mg, 0.57 mmol) was added thereto, and the mixture was stirred for 1 hour at room temperature. After completion of the reaction, the reaction solution was diluted in methylene chloride and washed with a saturated saline solution. The solution was dried over magnesium sulfate and the solvent was evaporated. Ethanol was added to the residue, which was heated to 70° C., dissolved and recrystallized by cooling the temperature to room temperature, thereby obtaining 130 mg of 2-(3,4-dimethoxybenzamide)-6-chlorobenzothiazole in a yield of 68%.

$^1$H NMR (CDCl$_3$): δ10.15 (s, 1H), 7.83 (d, J=1.8 Hz, 1H), 7.63-7.45 (m, 3H), 7.36 (dd, J=1.8, 8.7 Hz, 1H), 6.91 (d, J=8.2 Hz, 1H), 3.96 (s, 3H), 3.94 (s, 3H)

MS (ESI) Found: 349 [M+H]$^+$

KY02111

Using 3-(3,4-dimethoxyphenyl)propanoyl chloride (100 mg, 0.42 mmol) and 2-amino-6-chlorobenzothiazole (78 mg, 0.42 mmol) as substrates, the reaction was performed in the same manner as above, thereby obtaining 113 mg of 2-(3-(3,4-dimethoxyphenyl)propanamide)-6-chlorobenzothiazole in a yield of 72%.

$^1$H NMR (CDCl$_3$): δ9.41 (s, 1H), 7.79 (d, J=2.9 Hz, 1H), 7.62 (d, J=11.7 Hz, 1H), 7.37 (dd, J=2.6, 11.4 Hz, 1H), 6.80-6.67 (m, 3H), 3.85 (s, 3H), 3.82 (s, 3H), 3.03 (t, J=9.9 Hz, 2H), 2.77 (t, J=9.9 Hz, 2H)

MS (ESI) Found: 399 [M+H]$^+$

KY02114

Using 4-(3,4-dimethoxyphenyl)butanoyl chloride (100 mg, 0.41 mmol) and 2-amino-6-chlorobenzothiazole (76 mg, 0.41 mmol) as substrates, the reaction was performed in the same manner as above, thereby obtaining 121 mg of 2-(4-(3,4-dimethoxyphenyl)butanamide)-6-chlorobenzothiazole in a yield of 75%.

$^1$H NMR (CDCl$_3$): δ9.15 (s, 1H), 7.79 (d, J=2.9 Hz, 1H), 7.64 (d, J=11.3 Hz, 1H), 7.39 (dd, J=2.6, 11.4 Hz, 1H), 6.80-6.68 (m, 3H), 3.87 (s, 3H), 3.84 (s, 3H), 2.67 (t, J=9.9 Hz, 2H), 2.48 (t, J=9.9 Hz, 2H), 2.09 (m, 2H)

MS (ESI) Found: 413 [M+H]$^+$

KY01045

Using 5-(3,4-dimethoxyphenyl)pentanoyl chloride (30 mg, 0.13 mmol) and 2-amino-6-chlorobenzothiazole (23 mg, 0.13 mmol) as substrates, the reaction was performed in the same manner as above, thereby obtaining 39 mg of 2-(5-(3, 4-dimethoxyphenyl)pentanamide)-6-chlorobenzothiazole in a yield of 75%.

$^1$H NMR (CDCl$_3$): δ8.91 (s, 1H), 7.79 (d, J=8.7 Hz, 1H), 7.66 (d, J=8.7 Hz, 1H), 7.49 (dd, J=2.3, 8.7 Hz, 1H), 6.79 (d, J=7.8 Hz, 1H), 6.71 (d, J=7.8 Hz, 1H) 6.70 (s, 1H), 3.87 (s, 3H), 3.86 (s, 3H), 2.62 (t, J=7.4 Hz, 2H), 2.52 (t, J=7.3 Hz, 2H), 1.80 (m, 2H), 1.72 (m, 2H)

MS (ESI) Found: 405 [M+H]$^+$

KY01040

Using 3,4-dimethoxybenzoylyl chloride (100 mg, 0.5 mmol) and 2-amino-6-nitrobenzothiazole (105 mg, 0.57 mmol) as substrates, the reaction was performed in the same manner as above, thereby obtaining 100 mg of 2-(3,4-dimethoxybenzamide)-6-nitrobenzothiazole in a yield of 56%.

$^1$H NMR (CDCl$_3$): δ10.15 (s, 1H), 8.80 (d, J=2.3 Hz, 1H), 8.31 (dd, J=2.3, 9.2 Hz, 1H), 7.73 (d, J=9.2 Hz, 1H), 7.63-7.47 (m, 2H), 6.95 (d, J=8.7 Hz, 1H), 3.98 (s, 3H), 3.97 (s, 3H)

MS (ESI) Found: 360 [M+H]$^+$

KY02109

Using 2-(3,4-dimethoxyphenyl)acetyl chloride (100 mg, 0.51 mmol) and 2-amino-6-chlorobenzothiazole (94 mg, 0.51 mmol) as substrates, the reaction was performed in the same manner as above, thereby obtaining 153 mg of 2-(2-(3,4-dimethoxyphenyl)acetamide)-6-chlorobenzothiazole in a yield of 83%.

$^1$H NMR (CDCl$_3$): δ8.91 (s, 1H), 8.75 (s, 1H), 8.31 (dd, J=12.1 Hz, 1H), 7.77 (d, J=11.7 Hz, 1H), 7.00-6.70 (m, 3H), 3.92 (s, 3H), 3.90 (s, 3H), 3.86 (s, 2H)

MS (ESI) Found: 396 [M+H]$^+$

KY01042

Using 3-(3,4-dimethoxyphenyl)propanoyl chloride (100 mg, 0.5 mmol) and 2-amino-6-nitrobenzothiazole (105 mg, 0.57 mmol) as substrates, the reaction was performed in the same manner as above, thereby obtaining 138 mg of 2-(3-(3, 4-dimethoxyphenyl) propanamide)-6-nitrobenzothiazole in a yield of 71%.

$^1$H NMR (CDCl$_3$): δ9.29 (s, 1H), 8.75 (d, J=1.8 Hz, 1H), 8.31 (dd, J=2.3, 9.2 Hz, 1H), 7.77 (d, J=9.2 Hz, 1H), 6.80 (d, J=8.7 Hz, 1H), 6.75 (d, J=8.7 Hz, 1H), 6.74 (s, 1H), 3.85 (s, 3H), 3.84 (s, 3H), 3.06 (t, J=7.3 Hz, 2H), 2.83 (t, J=7.3 Hz, 2H)

MS (ESI) Found: 388 [M+H]$^+$

KY01043

Using 4-(3,4-dimethoxyphenyl)butanoyl chloride (55 mg, 0.25 mmol) and 2-amino-6-nitrobenzothiazole (50 mg, 0.25 mmol) as substrates, the reaction was performed in the same manner as above, thereby obtaining 65 mg of 2-(4-(3,4-dimethoxyphenyl) butanamide)-6-nitrobenzothiazole in a yield of 66%.

$^1$H NMR (CDCl$_3$): δ8.75 (d, J=2.3 Hz, 1H), 8.29 (dd, J=2.3, 8.7 Hz, 1H), 7.70 (d, J=8.7 Hz, 1H), 6.75 (d, J=8.7 Hz, 1H), 6.67 (s, 1H), 6.66 (d, J=8.7 Hz, 1H), 3.83 (s, 3H), 3.83 (s, 3H), 2.66 (t, J=7.4 Hz, 2H), 2.54 (t, J=7.3 Hz, 2H), 2.11 (m, 2H)

MS (ESI) Found: 402 [M+H]$^+$

KY01046

Using 5-(3,4-dimethoxyphenyl)pentanoyl chloride (30 mg, 0.13 mmol) and 2-amino-6-nitrobenzothiazole (25 mg, 0.13 mmol) as substrates, the reaction was performed in the same manner as above, thereby obtaining 38 mg of 2-(5-(3, 4-dimethoxyphenyl)pentanamide)-6-nitrobenzothiazole in a yield of 70%.

$^1$H NMR (CDCl$_3$): δ8.94 (s, 1H), 8.75 (d, J=2.3 Hz, 1H), 8.32 (dd, J=2.3, 9.2 Hz, 1H), 7.81 (d, J=9.2 Hz, 1H), 6.80 (d, J=7.8 Hz, 1H), 6.72 (d, J=7.8 Hz, 1H) 6.71 (s, 1H), 3.88 (s, 3H), 3.86 (s, 3H), 2.63 (t, J=7.4 Hz, 2H), 2.56 (t, J=7.3 Hz, 2H), 1.82 (m, 2H), 1.73 (m, 2H)

MS (ESI) Found: 416 [M+H]$^+$

KY02104

Using 2-(3,4-dimethoxyphenyl)acetyl chloride (100 mg, 0.51 mmol) and 2-amino-6-fluorobenzothiazole (86 mg, 0.51 mmol) as substrates, the reaction was performed in the same manner as above, thereby obtaining 157 mg of 2-(2-(3,4-dimethoxyphenyl)acetamide)-6-fluorobenzothiazole in a yield of 89%.

$^1$H NMR (CDCl$_3$): δ9.14 (s, 1H), 7.64 (dd, J=6.2, 12.1 Hz, 1H), 7.50 (dd, J=3.6, 11.0 Hz, 1H), 7.14 (ddt, J=3.7, 12.1 Hz, 1H), 6.90-6.78 (m, 3H), 3.90 (s, 3H), 3.87 (s, 3H), 3.80 (s, 2H)

MS (ESI) Found: 369 [M+H]$^+$

SO087

An N,N'-dimethylformamide (5 ml) solution containing 2-amino-6-bromobenzothiazole (500 mg, 2.18 mmol), 3-(3,4-dimethoxyphenyl)propionic acid (505 mg, 2.40 mmol), O-(6-chlorobenzotriazol-1-yl)-N,N,N',N'-tetramethyluronium hexafluorophosphate (1.09 g, 2.63 mmol) and N,N'-diisopropylethylamine (419 μl, 2.41 mmol) was stirred overnight at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was then evaporated. The residue was refluxed in ethanol and recrystallized, thereby obtaining 320 mg of 2-(3-(3,4-dimethoxyphenyl)propanamide)-6-bromobenzothiazole in a yield of 35%.

$^1$H NMR (DMSO-d$_6$): δ12.45 (s, 1H), 8.25 (d, J=1.8 Hz, 1H), 7.66 (d, J=8.4 Hz, 1H), 7.56 (dd, J=1.8, 8.4 Hz, 1H), 6.87-6.83 (m, 2H), 6.77-6.73 (m, 1H), 3.71 (s, 3H), 3.70 (s, 3H), 2.88 (t, J=7.0 Hz, 2H), 2.79 (t, J=7.0 Hz, 2H)

SO102

Using 2-amino-6-chlorobenzothiazole (55 mg, 0.298 mmol) and 3-(3,4-dimethoxyphenyl)propionic acid (80 mg, 0.357 mmol) as substrates, the reaction was performed in the same manner as SO087, thereby obtaining 40 mg of N-(6-chlorobenzothiazol-2-yl)-3-(4-ethoxy-3-methoxyphenyl) propanamide in a yield of 34%.

$^1$H NMR (DMSO-d$_6$): δ12.44 (s, 1H), 8.11 (d, J=2.2 Hz, 1H), 7.71 (d, J=8.8 Hz, 1H), 7.44 (dd, J=2.2, 8.8 Hz, 1H), 6.90-6.82 (m, 2H), 6.72 (dd, J=1.8, 7.0 Hz), 3.94 (q, J=7.0 Hz, 2H), 3.72 (s, 3H), 2.91-2.85 (m, 2H), 2.82-2.75 (m, 2H), 1.28 (t, J=7.0 Hz, 3H)

SO094

Sodium hydride (60%) (106 mg, 2.65 mmol) was added while stirring under ice cooling to an N,N'-dimethylformamide (7 ml) solution containing 2-amino-6-hydroxybenzothiazole (400 mg, 2.41 mmol) under an argon atmosphere and stirred for 30 minutes, and then 4-bromoethyl butyrate (521 μl, 3.62 mmol) was added thereto and stirred overnight at room temperature. After completion of the reaction, the reaction solution was diluted with ethyl acetate and washed with a saturated ammonium chloride aqueous solution and a saturated sodium chloride aqueous solution. The solution was dried over sodium sulfate and the solvent was evaporated, thereby obtaining 372 mg of ethyl 4-((2-aminobenzothiazol-6-yl) (oxy)butanoate in a yield of 55%.

An N,N'-dimethylformamide (5 ml) solution containing ethyl 4-((2-aminobenzothiazol-6-yl)oxy)butanoate (372 mg, 1.33 mmol), 3-(3,4-dimethoxyphenyl)propionic acid (335 mg, 1.59 mmol), O-(6-chlorobenzotriazol-1-yl)-N,N,N',N'- tetramethyluronium hexafluorophosphate (659 mg, 1.59 mmol) and N,N'-diisopropylethylamine (278 μl, 1.59 mmol) was stirred overnight at room temperature. After completion of the reaction, the reaction solution was diluted with ethyl acetate and washed with a saturated sodium hydrogen carbonate aqueous solution, distilled water and a saturated sodium chloride aqueous solution. The solution was dried over sodium sulfate and the solvent was evaporated. The residue was refluxed in ethanol and recrystallized, thereby obtaining 447 mg of ethyl 4-((2-(3-(3,4-dimethoxyphenyl)propanamide)benzothiazol-6-yl)oxy)butanoate in a yield of 76%.

5 N NaOH Aqueous solution (378 μl) was added to a 1,4-dioxane solution containing ethyl 4-((2-(3-(3,4-dimethoxyphenyl)propanamide)benzothiazol-6-yl)oxy)butanoate (447 mg, 0.946 mmol) and stirred overnight at room temperature. After completion of the reaction, the reaction solution was condensed and neutralized with 6 N hydrochloric acid under ice cooling. The deposit was collected by vacuum filtration and washed with water, thereby obtaining 271 mg of 4-((2-(3-(3,4-dimethoxyphenyl)propanamide)benzothiazol-6-yl)oxy)butanoic acid in a yield of 64%.

1-Hydroxybenzotriazole (38 mg, 0.248 mmol) and 1-ethyl-3-(3-dimethylaminopropyl)carbodiimide hydrochloride (52 mg, 0.270 mmol) were added to an N,N'-dimethylformamide (1 ml) solution containing 4-((2-(3-(3,4-dimethoxyphenyl)propanamide)benzothiazol-6-yl)oxy) butanoic acid (100 mg, 0.225 mmol) and morpholine (22 μl, 0.248 mmol) and stirred for 2 days at room temperature. After completion of the reaction, the reaction solution was diluted with ethyl acetate and washed with saturated sodium hydrogen carbonate aqueous solution, distilled water and a saturated sodium chloride aqueous solution. The solution was dried over sodium sulfate and the solvent was evaporated. The residue was refluxed in ethanol and recrystallized, thereby obtaining 50 mg of 3-(3,4-dimethoxyphenyl)-N-(6-(4-morpholino-4-oxobutoxy)benzothiazol-2-yl)propanamide in a yield of 43%.

$^1$H NMR (DMSO-$d_6$): δ12.20 (s, 1H), 7.60 (d, J=8.8 Hz, 1H), 7.55 (d, J=2.6 Hz, 1H), 7.01 (dd, J=2.6, 8.8 Hz, 1H), 6.86-6.83 (m, 2H), 6.75 (dd, J=1.8, 8.1 Hz), 4.03 (t, J=6.2 Hz, 2H), 3.71 (s, 3H), 3.70 (s, 3H), 3.56-3.53 (m, 4H), 3.46-3.42 (m, 4H), 2.87 (t, J=7.0 Hz), 2H), 2.75 (t, J=7.0 Hz, 2H), 2.51-2.46 (m, 2H), 1.96 (t, J=7.0 Hz, 2H)

SO096

Using 4-((2-(3-(3,4-dimethoxyphenyl)propanamide)benzothiazol-6-yl)oxy)butanoic acid (80 mg, 0.180 mmol) and 1-methylpiperazine (21.8 μl, 0.198 mmol) as substrates, the reaction was performed in the same manner as SO094, thereby obtaining 39 mg of 3-(3,4-dimethoxyphenyl)-N-(6-(4-(4-methylpiperazin-1-yl)-4-oxobutoxy)benzothiazol-2-yl)propanamide in a yield of 41%.

$^1$H NMR (DMSO-$d_6$): δ12.20 (br s, 1H), 7.54 (d, J=8.8 Hz, 1H), 7.48 (d, J=2.6 Hz, 1H), 6.96 (dd, J=2.6, 8.8 Hz, 1H), 6.86-6.82 (m, 2H), 6.73 (dd, J=1.8, 8.1 Hz, 1H), 4.01 (t, J=6.2 Hz, 2H), 3.71 (s, 3H), 3.69 (s, 3H), 3.45-3.41 (m, 4H), 2.86 (t, J=7.7 Hz, 2H), 2.70 (t, J=7.7 Hz, 2H), 2.50-2.45 (m, 2H), 2.29-2.20 (m, 4H), 2.15 (s, 3H), 1.94 (t, J=7.0 Hz, 2H)

The invention claimed is:
1. A method for inducing differentiation of pluripotent stem cells into cardiac muscle cells which comprises in vitro culturing pluripotent stem cells in a medium containing a compound represented by Formula (I)

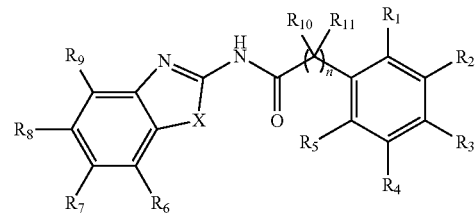

[Formula 1]

wherein
$R_1$ to $R_5$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_1$ to $R_5$ may join together to form —O—$CH_2$—O— or —O—$(CH_2)_2$—O—, $R_6$ to $R_9$ are each independently a hydrogen atom; a halogen atom; a hydroxyl group; a linear or branched alkoxy group having 1 to 5 carbon atoms; a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom, a linear or branched alkyl group having 1 to 5 carbon atoms which is unsubstituted or substituted with a halogen atom; or a group —$NR_{12}R_{13}$ wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—$CH_2$—O— or —O—$(CH_2)_2$—O—, $R_{10}$ to $R_{11}$ are each independently a hydrogen atom; or a linear or branched alkyl group having 1 to 5 carbon atoms, X is —$CR_{14}$, wherein $R_{14}$ is a hydrogen atom, a halogen atom, a hydroxyl group, a linear or branched alkoxy group having 1 to 5 carbon atoms, or a linear or branched alkyl group having 1 to 5 carbon atoms which is unsubstituted or substituted with a halogen atom; an oxygen atom; a sulfur atom; a selenium atom; or a group —$NR_{15}$, wherein $R_{15}$ is a hydrogen atom, a linear or branched alkyl group having 1 to 5 carbon atoms, or a linear or branched acyl group having 1 to 5 carbon atoms, and n is an integer of 0 to 6, or a salt thereof 2. The method according to claim 1, wherein
$R_6$ to $R_9$ are each independently a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —$NR_{12}R_{13}$, wherein $R_{12}$ and $R_{13}$ are each independently a hydrogen atom, an oxygen atom, or a linear or branched alkyl group having 1 to 5 carbon atoms which is unsubstituted or substituted with a halogen atom; wherein two adjacent groups among $R_6$ to $R_9$ may join together to form —O—CH$_2$—O— or —O—(CH$_2$)$_2$—O—.

3. The method according to claim 2, wherein $R_1$ to $R_5$ are each independently a hydrogen atom; a halogen atom; a hydroxy group; a linear or branched alkoxy group having 1 to 5 carbon atoms; or a linear or branched alkyl group having 1 to 5 carbon atoms which is unsubstituted or substituted with a halogen atom; wherein two adjacent groups among $R_1$ to $R_5$ may join together to form —O—CH$_2$—O— or —O—(CH$_2$)$_2$—O—, and X is an oxygen atom:, a sulfur atom; or a group —NR$_{15}$, wherein R$_{15}$ is a hydrogen atom, a linear or branched alkyl group having 1 to 5 carbon atoms, or a linear or branched acyl group having 1 to 5 carbon atoms.

4. The method according to claim 3, wherein $R_2$ and $R_3$ are a linear or branched alkoxy group having 1 to 5 carbon atoms, or $R_2$ and $R_3$ join together to form —O—CH$_2$—O— or —O—(CH$_2$)$_2$—O—, $R_6$ and $R_9$ are each independently, a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, and $R_7$ is a hydrogen atom; a halogen atom; a hydroxyl group; a linear or branched alkoxy group having 1 to 5 carbon atoms; a linear or branched alkyl group having 1 to 5 carbon atoms which is unsubstituted or substituted with a halogen atom; or a group —NR$_{12}$R$_{13}$, wherein R$_{12}$ and R$_{13}$ are each independently a hydrogen atom, an oxygen atom, or a linear or branched alkyl group having 1 to 5 carbon atoms which is unsubstituted or substituted with a halogen atom, $R_8$ is a hydrogen atom; a halogen atom; a hydroxyl group; a linear or branched alkoxy group having 1 to 5 carbon atoms; or a linear or branched alkyl group having 1 to 5 carbon atoms which is unsubstituted or substituted with a halogen atom, or $R_7$ and $R_8$ join together to form —O—CH$_2$—O— or —O—(CH$_2$)$_2$—O—.

5. The method according to claim 4, wherein $R_1$, $R_4$, $R_5$, $R_6$ and $R_9$ are a hydrogen atom, $R_2$ and $R_3$ are a methoxy group, an ethoxy group or a propoxy group, and $R_{10}$ and $R_{11}$ are a hydrogen atom.

6. The method according to claim 5, wherein

X is a sulfur atom, and n is an integer of 0 to 4.

7. The method according to claim 1, wherein $R_1$, $R_4$, $R_5$, $R_6$, $R_8$ and $R_9$ are each independently a hydrogen atom; a halogen atom; a hydroxy group; a linear or branched alkoxy group having 1 to 5 carbon atoms; or a linear or branched alkyl group having 1 to 5 carbon atoms which is unsubstituted or substituted with a halogen atom;

$R_2$ and $R_3$ are a linear or branched alkoxy group having 1 to 5 carbon atoms, or $R_2$ and $R_3$ join together to form —O—CH$_2$—O— or —O—(CH$_2$)$_2$—O—, $R_7$ is a linear or branched alkoxy group having 1 to 5 carbon atoms which is substituted with a group —C(O)A, wherein A is a saturated or unsaturated 5- or 6-membered ring which is unsubstituted or substituted with a linear or branched alkyl group having 1 to 5 carbon atoms and the ring may contain 1 or 2 atoms independently selected from a nitrogen atom, an oxygen atom and a sulfur atom; and X is an oxygen atom; a sulfur atom; or a group —NR$_{15}$, wherein R15 is a hydrogen atom, a linear or branched alkyl group having 1 to 5 carbon atoms, or a linear or branched acyl group having 1 to 5 carbon atoms.

8. The method according to claim 7, wherein $R_1$, $R_4$, $R_5$, $R_6$, $R_8$, and $R_9$ are a hydrogen atom, $R_2$ and $R_3$ are a methoxy group, an ethoxy group or a propoxy group, $R_{10}$ and $R_{11}$ are a hydrogen atom, X is a sulfur atom, A is a piperidinyl group, a piperazinyl group or a morpholinyl group which is unsubstituted or substituted with a linear or branched alkyl group having 1 to 5 carbon atoms, and n is an integer of 0 to 4.

9. The method according to claim 1, wherein the compound is selected from:

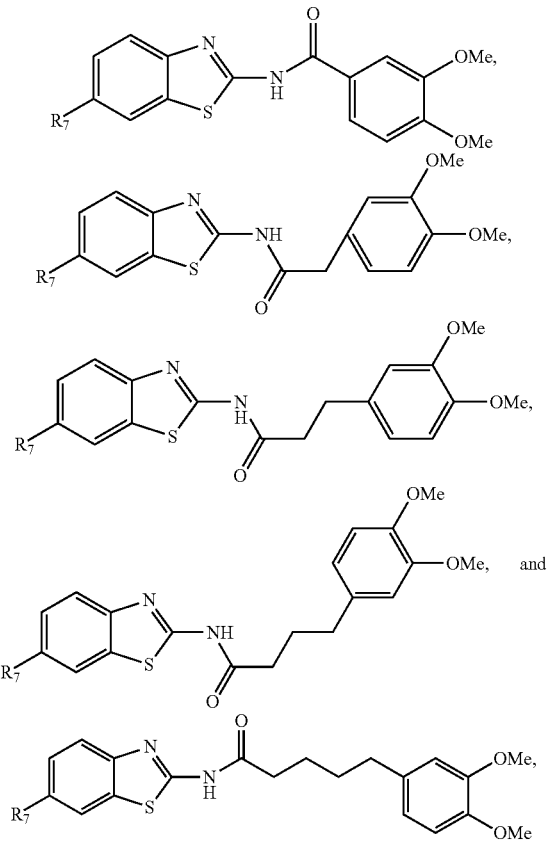

wherein $R_7$ is a halogen.

10. The method according to claim 1, wherein the pluripotent stem cells are mammalian cells.

11. The method according to claim 10, wherein the pluripotent stem cells are primate cells.

12. The method according to claim 1, which is used in combination with a different cardiac muscle cell differentiation promoter.

13. The method according to claim 12, wherein the different cardiac muscle cell differentiation promoter is nitrovin; a combination of bFGF, BMP4, VEGF, DKK1 and Activin A; or a Wnt signaling inhibitor.

14. The method according to claim 1, wherein the compound is selected from:
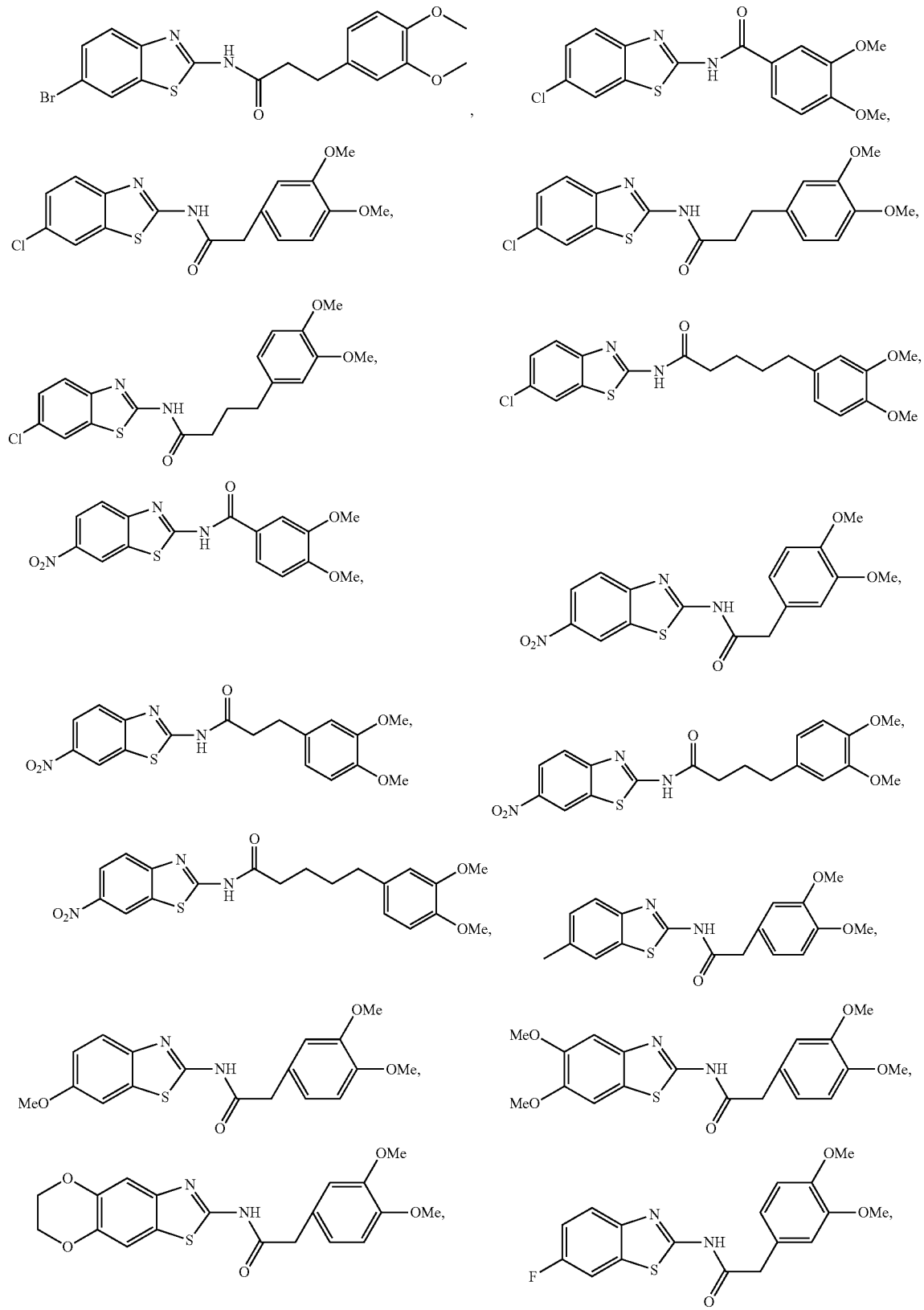

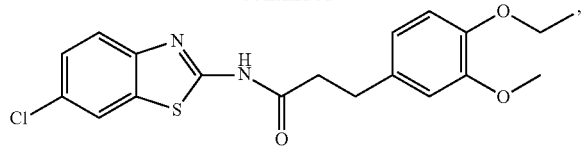
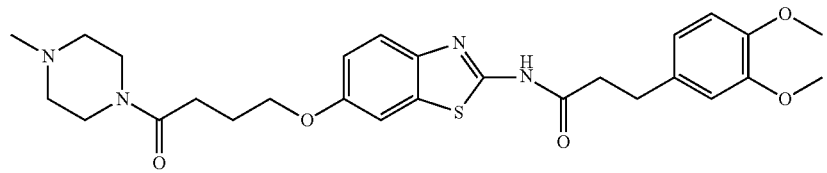
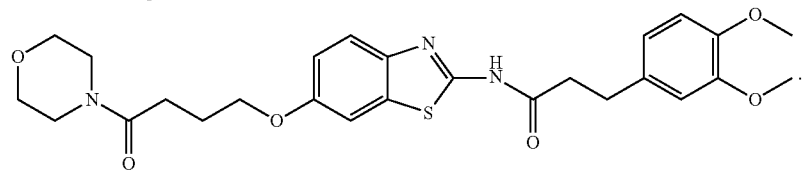
15. The method of claim 1 wherein R1, R4, R5, R6, R8, R9, R10, and R11 are a hydrogen atom, R2 and R3 are independently a methoxy group, an ethoxy group, or a propoxy group, R7 is a halogen atom, X is a sulfur atom, and n is an integer of 0 to 4.
* * * * *